(12) United States Patent
Takeda

(10) Patent No.: US 10,768,778 B2
(45) Date of Patent: Sep. 8, 2020

(54) INFORMATION PROCESSING APPARATUS, INFORMATION PROCESSING METHOD, AND COMPUTER PROGRAM

(71) Applicant: Sony Corporation, Tokyo (JP)

(72) Inventor: Yasuhiro Takeda, Tokyo (JP)

(73) Assignee: SONY CORPORATION, Tokyo (JP)

( * ) Notice: Subject to any disclaimer, the term of this patent is extended or adjusted under 35 U.S.C. 154(b) by 251 days.

(21) Appl. No.: 15/274,488

(22) Filed: Sep. 23, 2016

(65) Prior Publication Data

US 2017/0010784 A1 Jan. 12, 2017

Related U.S. Application Data

(63) Continuation of application No. 14/065,633, filed on Oct. 29, 2013.

(30) Foreign Application Priority Data

Dec. 25, 2012 (JP) .................................. 2012-280739

(51) Int. Cl.
*G06F 3/0481* (2013.01)
*G06F 3/0482* (2013.01)
*G06F 19/00* (2018.01)

(52) U.S. Cl.
CPC ........ *G06F 3/04817* (2013.01); *G06F 3/0482* (2013.01); *G06F 19/3475* (2013.01)

(58) Field of Classification Search
CPC .... G06F 3/048; G06F 3/04817; G06F 3/0482; G06F 19/34; G06F 19/3475
See application file for complete search history.

(56) References Cited

U.S. PATENT DOCUMENTS 5,673,691 A * 10/1997 Abrams ................ G06F 15/025
600/300
6,553,386 B1 4/2003 Alabaster
(Continued)

FOREIGN PATENT DOCUMENTS

| CN | 102314557 A | 1/2012 |
| CN | 102752447 A | 10/2012 |

(Continued)

OTHER PUBLICATIONS

Owen Williams, Slack invents emoji fays: A whole new way what you think ???, 97/09/2015, 2015, 5 Pages https://thenextweb.com/apps/2015/07/09/how-did-we-ever-live-without-this/ (Year: 2015).*

(Continued)

*Primary Examiner* — Ryan Barrett
*Assistant Examiner* — Parmanand D Patel
(74) *Attorney, Agent, or Firm* — Xsensus LLP

(57) ABSTRACT

There is provided an information processing apparatus, including an icon display section which displays an icon associated to an action of a user for a purpose of the user, a selection condition acquisition section which acquires a selection condition of the icon displayed by the icon display section, and a display information generation section which generates display information for sharing selected action associated to the icon with another user by using the selection condition acquired by the selection condition acquisition section.

20 Claims, 28 Drawing Sheets

(56) References Cited

U.S. PATENT DOCUMENTS

| | | | |
|---|---|---|---|
| 7,949,506 B1* | 5/2011 | Hill | G06F 19/00 703/11 |
| 8,015,076 B2 | 9/2011 | Owens | |
| 8,640,257 B1* | 1/2014 | Sherrets | G06F 21/6245 707/732 |
| 2004/0210435 A1* | 10/2004 | Oshima | G06F 17/2735 704/10 |
| 2005/0209887 A1* | 9/2005 | Pollner | G06Q 30/02 705/3 |
| 2006/0089840 A1* | 4/2006 | May | G06F 19/00 715/224 |
| 2007/0179359 A1 | 8/2007 | Goodwin | |
| 2007/0247642 A1 | 10/2007 | Nakamura | |
| 2010/0062905 A1* | 3/2010 | Rottler | G06F 19/3481 482/9 |
| 2010/0136508 A1 | 6/2010 | Zekhtser | |
| 2011/0159469 A1* | 6/2011 | Hwang | A61B 5/4872 434/247 |
| 2013/0138230 A1* | 5/2013 | Landers | G06F 17/40 700/91 |

FOREIGN PATENT DOCUMENTS

| | | |
|---|---|---|
| EP | 2 672 476 A1 | 12/2013 |
| JP | 2002-236756 A | 8/2002 |
| JP | 2005-111178 A | 4/2005 |
| JP | 2009-116731 A | 5/2009 |
| JP | 2009-175963 A | 8/2009 |
| JP | 2010-250437 | 11/2010 |
| JP | 2012-143601 | 8/2012 |
| JP | 2012-143601 A | 8/2012 |

OTHER PUBLICATIONS

Matt Silverman, Reddit: A Beginner's Guide, Jun. 6, 2012, 9 Pages https://web.archive.org/web/20120606181040/https://mashable.com/2012/06/06/reddit-for-beginners/ (Year: 2012).*

Robbie Gonzalez, The Surprisingly Complex Design of Facebook's New Emoji, Oct. 12, 2015, 7 Pages https://www.wired.com/2015/10/facebook-reactions-design/ (Year: 2015).*

Japanese Office Action dated Jul. 26, 2016 in Japanese Patent Application No. 2012-280739.

Combined Office Action and Search Report dated Jan. 26, 2017 in Chinese Patent Application No. 201310698716.9 (with English language translation).

Shi-tian Zhao, "The design and implementation of based on the Android platform movement auxiliary software" Chinese Master's Theses Full-text Database, Information Science and Technology, Apr. 15, 2012, 8 Pages (with Partial English language translation).

Office Action dated Feb. 16, 2016 in Japanese Patent Application No. 2012-280739. (4pgs.).

Japanese Office Action dated Jan. 17, 2017 in Patent Application No. 2016-075553 (without English Translation).

Japanese Office Action dated Dec. 1, 2016 in Patent Application No. 2012-280739 (without English Translation).

Combined Chinese Office Action and Search Report dated Oct. 11, 2017 in Patent Application No. 201310698716.9 (with English Translation).

Office Action dated Aug. 22, 2017 in Japanese Patent Application No. 2016-075553.

Office Action dated Aug. 29, 2017 in Japanese Patent Application No. 2012-280739.

* cited by examiner

INFORMATION PROCESSING APPARATUS, INFORMATION PROCESSING METHOD, AND COMPUTER PROGRAM

CROSS REFERENCE TO RELATED APPLICATIONS

This application is a continuation application of, and claims the benefit of priority under 35 U.S.C. § 120 from, U.S. application Ser. No. 14/065,633, filed Oct. 29, 2013, which claims the benefit of priority under 35 U.S.C. § 119 from Japanese Priority Patent Application JP 2012-280739 filed Dec. 25, 2012. The entire contents of each of the above applications are incorporated herein by reference.

BACKGROUND

The present disclosure relates to an information processing apparatus, an information processing method, and a computer program.

There are various activities, such as studying, playing sports or dieting, which are continuously performed by people. Accordingly, technology has been considered and disclosed (for example, refer to JP 2010-250437A) for continuing activities which have been started by people.

SUMMARY

However, while it is easy for a user with a strong will to continuously perform an activity which has been started with a temporary objective, an activity which has been started with a temporary objective will not be continued by a user without a strong will, a so-called person with no power of perseverance. By considering this point, technology has been sought after for maintaining or improving motivation of an activity which has been started by a user with a temporary objective, in order for this activity to be continuously performed without the user becoming a person with no power of perseverance.

Accordingly, the present disclosure provides a new and improved information processing apparatus, information processing method, and computer program capable of maintaining or improving motivation to continue an activity which has been temporarily started by a user, in order for this activity to be continuously performed by the user.

According to an embodiment of the present disclosure, there is provided an information processing apparatus, including an icon display section which displays an icon associated to an action of a user for a purpose of the user, a selection condition acquisition section which acquires a selection condition of the icon displayed by the icon display section, and a display information generation section which generates display information for sharing selected action associated to the icon with another user by using the selection condition acquired by the selection condition acquisition section.

According to an embodiment of the present disclosure, there is provided an information processing method, including displaying an icon associated to an action for a purpose of a user, acquiring a selection condition of the displayed icon, and generating display information for sharing selected action associated to the icon with another user by using the acquired selection condition.

According to an embodiment of the present disclosure, there is provided a computer program for causing a computer to execute displaying an icon associated to an action for a purpose of a user, acquiring a selection condition of the displayed icon, and generating display information for sharing selected action associated to the icon with another user by using the acquired selection condition.

According to the present disclosure such as described above, a new and improved information processing apparatus, information processing method, and computer program can be provided capable of maintaining or improving motivation to continue an activity which has been temporarily started by a user, in order for this activity to be continuously performed by the user.

DETAILED DESCRIPTION OF THE EMBODIMENT(S)

Figure 1:
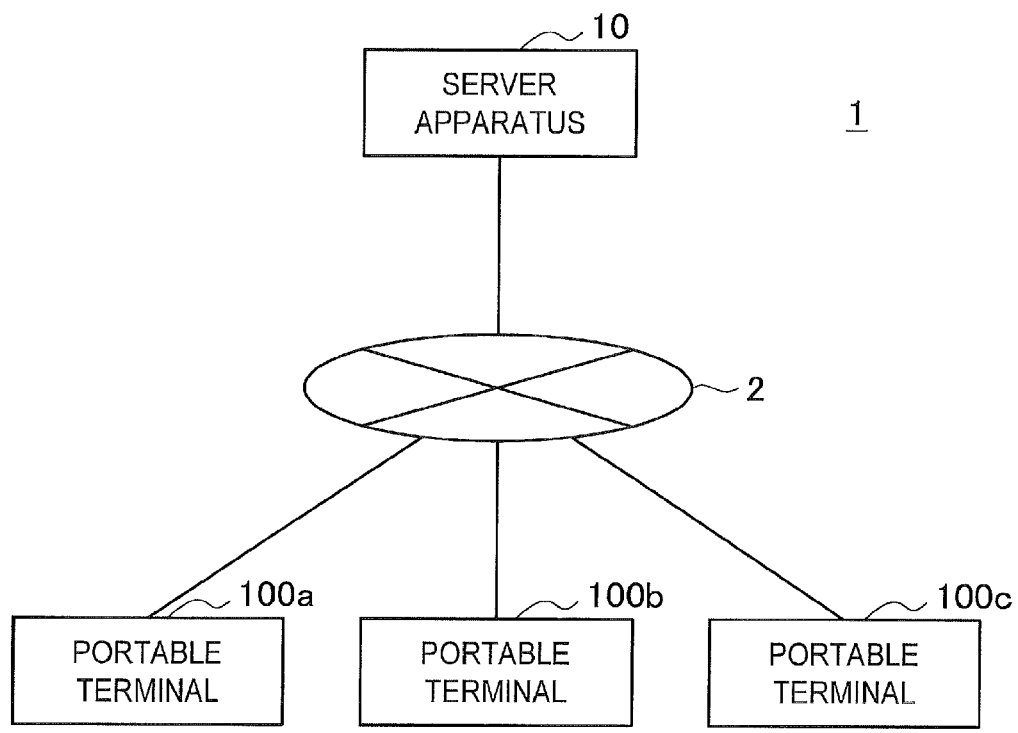
FIG. 1 is an explanatory diagram which shows a configuration example of an information processing system 1 according to an embodiment of the present disclosure.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

The description will be given in the following order.
<1. The embodiments of the present disclosure>
[System configuration example]
[Functional configuration example of the portable terminal]
[Functional configuration example of the server apparatus]
[Operation example of the portable terminal]
[Examples of information displayed on the portable terminal]
[Modified examples]
<2. Conclusion>

1. The Embodiments of the Present Disclosure

[System Configuration Example]

First, a configuration example of an information processing system according to an embodiment of the present disclosure will be described while referring to the figures. FIG. 1 is an explanatory diagram which shows a configuration example of an information processing system 1 according to an embodiment of the present disclosure. Hereinafter, a configuration example of the information processing system 1 according to an embodiment of the present disclosure will be described by using FIG. 1.

As shown in FIG. 1, the information processing system 1 according to an embodiment of the present disclosure includes a server apparatus 10, and portable terminals 100a, 100b and 100c. Further, as shown in FIG. 1, the server apparatus and the portable terminals 100a, 100b and 100c are connected via a network 2 such as the internet.

The server apparatus 10 retains data used by applications executed by the portable terminals 100a, 100b and 100c, which will be described later, and provides this data to the portable terminals 100a, 100b and 100c as necessary.

The portable terminals 100a, 100b and 100c are terminals which execute applications, which will be described later. While a case is shown in FIG. 1 where it is assumed that three users each use the portable terminals 100a, 100b and 100c, the present disclosure is not limited to such an example for the number of portable terminals. Further, in the following description, the portable terminals 100a, 100b and 100c will be collectively called a portable terminal 100 unless specifically noted. The portable terminal 100 may be, for example, a mobile phone, a multi-function mobile phone (a smartphone), a tablet type portable terminal, a mobile music player, a portable game machine, or the like.

In order for an activity, which has been temporarily started by a user, to be continuously executed by the portable terminal 100, the information processing system 1 according to an embodiment of the present disclosure executes an application for maintaining or improving motivation of this activity for the user. Further, data generated by the execution of the application by the portable terminal 100 is managed by the server apparatus 10.

In the following description, a case will be illustrated in which an application is executed by the portable terminal 100 so as to maintain or improve motivation for a diet, as an example of an activity for the user, in order to continuously perform this diet. Hereinafter, an application for maintaining or improving motivation for this diet will be called a "diet support application".

Heretofore, a configuration example of the information processing system 1 according to an embodiment of the present disclosure has been described by using FIG. 1. Next, a functional configuration example of the portable terminal 100 according to an embodiment of the present disclosure will be described.

[Functional Configuration Example of the Portable Terminal]

Figure 2:
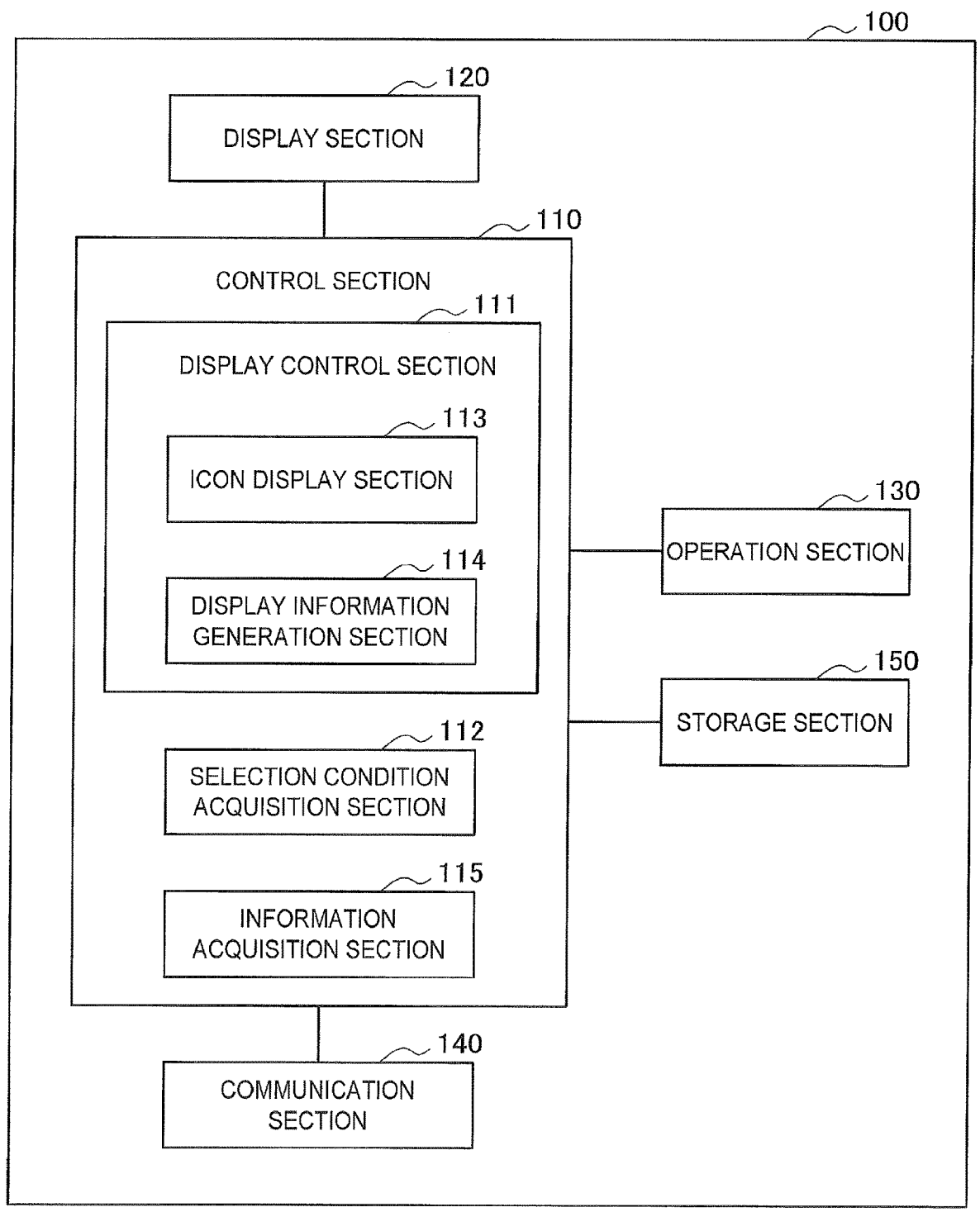
FIG. 2 is an explanatory diagram which shows a functional configuration example of a portable terminal 100 according to an embodiment of the present disclosure.

FIG. 2 is an explanatory diagram which shows a functional configuration example of the portable terminal 100 according to an embodiment of the present disclosure. Hereinafter, a functional configuration example of the portable terminal 100 according to an embodiment of the present disclosure will be described by using FIG. 2.

As shown in FIG. 2, the portable terminal 100 according to an embodiment of the present disclosure includes a control section 110, a display section 120, an operation section 130, a communication section 140, and a storage section 150.

The control section 110 is, for example, a CPU (Central Processing Unit), and controls the operations of the portable terminal 100. The control section 110 may control the operations of the portable terminal 100 by reading and sequentially executing computer programs stored in the storage section 150.

Also, as shown in FIG. 2, the control section 110 included in the portable terminal 100 according to an embodiment of the present disclosure includes a display control section 111, a selection condition acquisition section 112, and an information acquisition section 115.

The display control section 111 controls the display of information on the display section 120. Also, as shown in FIG. 2, the display control section 111 includes an icon display section 113 and a display information generation section 114.

When the diet support application is executed by the portable terminal 100, 10 the icon display section 113 controls the display of icons on the display section 120. While the details will be described later, when the diet support application is executed by the portable terminal 100, the icon display section 113 displays, on the display section 120, icons related to actions of the user which have been performed for the diet.

The display information generation section 114 generates display information for sharing actions related to selected icons with other users, based on a selection condition of the icons (for example, the selection frequency of the icons) by the selection condition acquisition section 112, which will be described later. An example of display information generated by the display information generation section 114 will be described later.

The selection condition acquisition section 112 counts the frequency at which the icons displayed on the display section 120 by the icon display section 113 are selected by the user of the portable terminal 100. Information of the selection condition of the icons (for example, the selection frequency of the icons) acquired by the selection condition acquisition section 112 is used in a generation process of display information by the display information generation section 114.

The information acquisition section 115 acquires information transmitted via the communication section 140, for example, from another apparatus. The control section 110 can project the information acquired from another apparatus by the information acquisition section 115 on the screen of icons by the icon display section 113.

The operation section 130 is included in the portable terminal 100 for allowing the user to operate the portable terminal 100, and is constituted by a keyboard, buttons or a touch panel, for example. In the following description, the operation section 130 will be described as an operation section which has a touch panel included in the display section 120. The communication section 140 performs communication with another apparatus via the network 2. The storage section 150 is constituted by a storage medium such as ROM or RAM, and stores computer programs for operating the portable terminal 100, and setting information used by the portable terminal 100 or these computer programs.

Heretofore, a functional configuration example of the portable terminal 100 according to an embodiment of the present disclosure has been described by using FIG. 2. Next, a functional configuration example of the server apparatus 10 according to an embodiment of the present disclosure will be described.

[Functional Configuration Example of the Server Apparatus]

Figure 3:
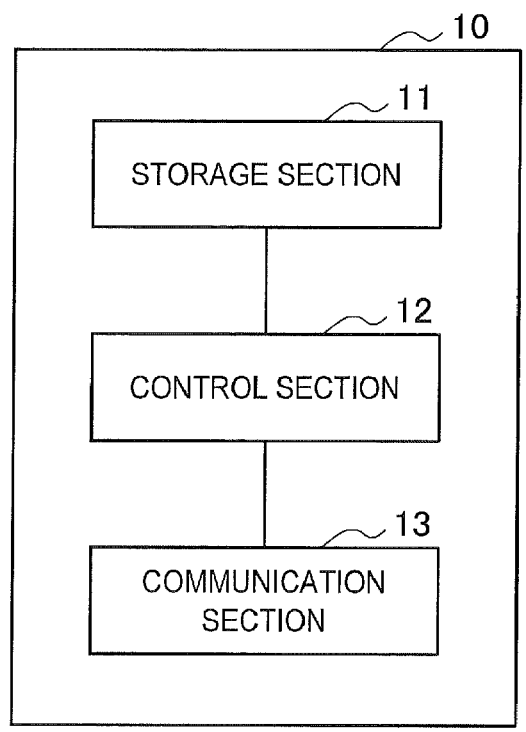
FIG. 3 is an explanatory diagram which shows a functional configuration example of a server apparatus 10 according to an embodiment of the present disclosure.

FIG. 3 is an explanatory diagram which shows a functional configuration example of the server apparatus 10 according to an embodiment of the present disclosure. The server apparatus 10 shown in FIG. 3 is a server apparatus which manages data used by the diet support application which is executed by the portable terminal 100. Hereinafter, a functional configuration example of the server apparatus 10 according to an embodiment of the present disclosure will be described by using FIG. 3.

As shown in FIG. 3, the server apparatus 10 according to an embodiment of the present disclosure includes a storage section 11, a control section 12, and a communication section 13.

The storage section 11 is constituted by a hard disk device, for example, and stores data used by the diet support application executed by the portable terminal 100. For example, there is registration information of the user who uses the diet support application, and information related to the selection condition of the icons by the user of the diet support application, as data used by the diet support application executed by the portable terminal 100.

The control section 12 is a CPU, for example, and controls the operations of the server apparatus 10. For example, the control section 12 reads data stored in the storage section 11, in accordance with a request from the portable terminal 100 via the network 2, and provides the read data to the portable terminal 100. The communication section 13 executes communication with another apparatus (that is, the portable terminal 100) via the network 2.

Heretofore, a functional configuration example of the server apparatus 10 according to an embodiment of the present disclosure has been described by using FIG. 3. Next, an operation example of the portable terminal 100 according to an embodiment of the present disclosure will be described.

[Operation Example of the Portable Terminal]

Figure 4:
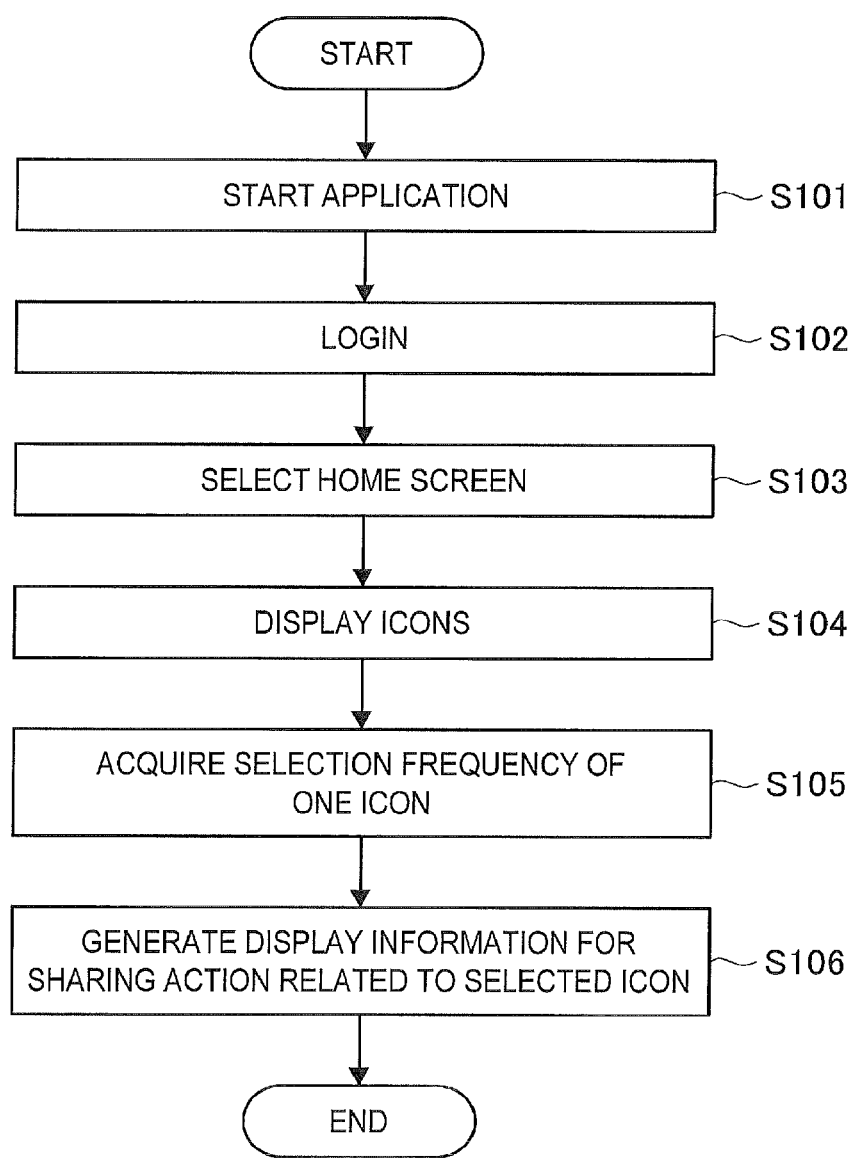
FIG. 4 is a flow chart which shows an operation example of the portable terminal 100 according to an embodiment of the present disclosure.

FIG. 4 is a flow chart which shows an operation example of the portable terminal 100 according to an embodiment of the present disclosure. The flow chart shown in FIG. 4 is an operation example of the portable terminal 100 at the time when the portable terminal 100 executes the diet support application. Hereinafter, an operation example of the portable terminal 100 according to an embodiment of the present disclosure will be described by using FIG. 4.

When the diet support application installed in the portable terminal 100 is started by the user of the portable terminal 100 (step S101), a screen of the diet support application is displayed on the display section 120 of the portable terminal 100. Then, the portable terminal 100 executes a login process using the started diet support application in accordance with an operation of the user (or automatically after it has started) (step S102). The login process of step S102 is executed, for example, by the control section 110 communicating with the server apparatus 10.

A design example of a login screen for the diet support application will be described later. Further, the login process by the above described step S102 is not particularly limited, and for example, an authentication process may be performed by allowing the user to input a user ID and password, or an authentication process may be performed by collaborating with other Web services.

When the login process by the above described step S102 is executed, and authenticates the user, it becomes possible for the portable terminal 100 to provide the user with a service by the started diet support application. While a screen transition example of the diet support application executed by the portable terminal 100 will be described in detail later, when the login process is completed, the diet support application operates so as to display a menu screen. Then, by a user operation, the diet support application operates so as to transition to a home screen for registering actions related to the diet executed by this user.

When a display for the home screen of the diet support application is selected by an operation by the user of the portable terminal 100 (step S103), the portable terminal 100 displays the home screen of the diet support application. At the time when the home screen of the diet support application is displayed, the portable terminal 100 displays, on the home screen, icons corresponding to the actions related to the diet performed by the user (step S104). The display process of icons of step S104 is executed, for example, by the icon display section 113.

When icons corresponding to actions related to the diet performed by the user are displayed on the home screen in the above described step S104, the portable terminal 100 can allow the user to select the icons displayed on the home screen. When the user selects an icon displayed on the home screen, the portable terminal 100 acquires a selection frequency of the icon, as a selection condition of the icon by this user (step S105). The acquisition process for the selection frequency of icons of step S105 is executed, for example, by the selection condition acquisition section 112.

When the selection frequency of the icon selected by the user is acquired by the above described step S105, to continue, the portable terminal 100 generates display information for sharing, with other users, an action related to the diet which relates to this icon, based on information of the acquired selection frequency (step S106). The generation of the display information of step S106 is generated, for example, by the display information generation section 114. Further, the generation of the display information of step S106 may not necessarily be executed immediately after the acquisition of the selection frequency of the above described step S105. For example, the generation of the display information of step S106 may be executed at the time when displaying a timeline screen, which will be described later.

Since an activity which has been temporarily started by the user is continuously executed, by executing operations such as those shown in FIG. 4, it becomes possible for the portable terminal 100 according to an embodiment of the present disclosure to maintain or improve motivation of this activity for the user by sharing, with other users, information based on the frequency of actions for this activity performed by the user.

Note that a shared range of actions performed by the user may be set as a shared range for all of the users who use the diet support application, or may be set as a shared range for some of the users who use the diet support application.

Heretofore, an operation example of the portable terminal 100 according to an embodiment of the present disclosure has been described by using FIG. 4. To continue, the operations of the portable terminal 100 according to an embodiment of the present disclosure will be described in more detail, while showing examples of information displayed on the display section 120.

[Examples of Information Displayed on the Portable Terminal]

Figure 5:
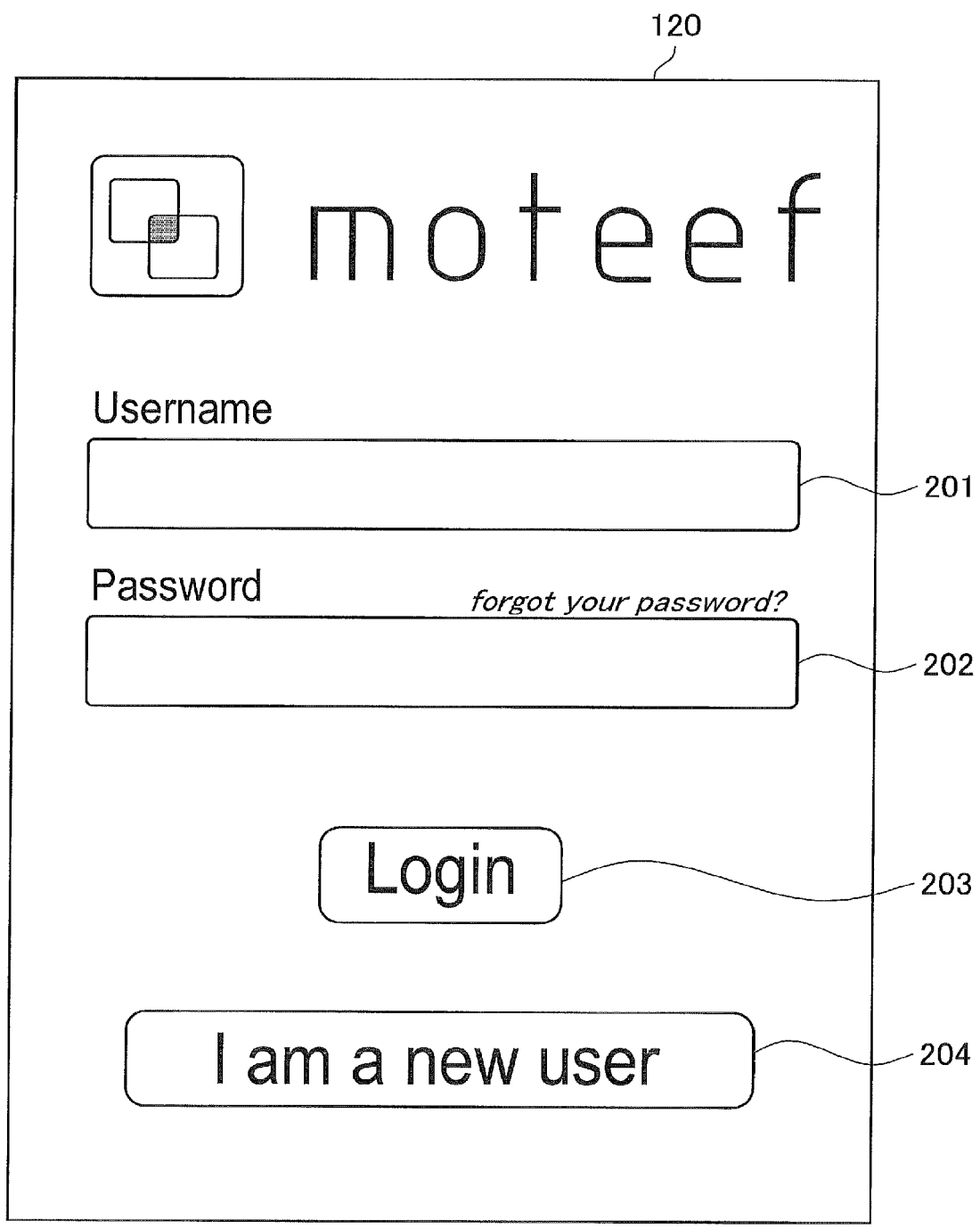
FIG. 5 is an explanatory diagram which shows an example of information displayed on a display section 120.

FIG. 5 is an explanatory diagram which shows an example of information displayed on a display section 120 of the portable terminal 100. The explanatory diagram shown in FIG. 5 is an example of a login screen initially displayed at the time when the diet support application installed in the portable terminal 100 is started by the user.

A username input area 201 for allowing the user to input a username, and a password input area 202 for allowing the user to input a password, are displayed on the login screen of the diet support application shown in FIG. 5. Also, a login button 203 for logging in with the username input in the username input area 201 and the password input in the password input area 202, and a new user registration button 204 for registering a new user, are displayed on the login screen of the diet support application shown in FIG. 5.

The user of the portable terminal 100 can input a username and a password in the username input area 201 and the password input area 202, respectively, by operating the operation section 130, and can log in to a service provided by the diet support application, by selecting the login button 203. The diet support application executed by the portable terminal 100 executes a login process by the collation of user information registered in the server apparatus 10. Further, if the user of the portable terminal 100 is not a registered user, it becomes possible to register a new user who uses the diet support application, by selecting the new user registration button 204. Note that a detailed description for the registration of a new user who uses the diet support application will be omitted.

Figure 6:
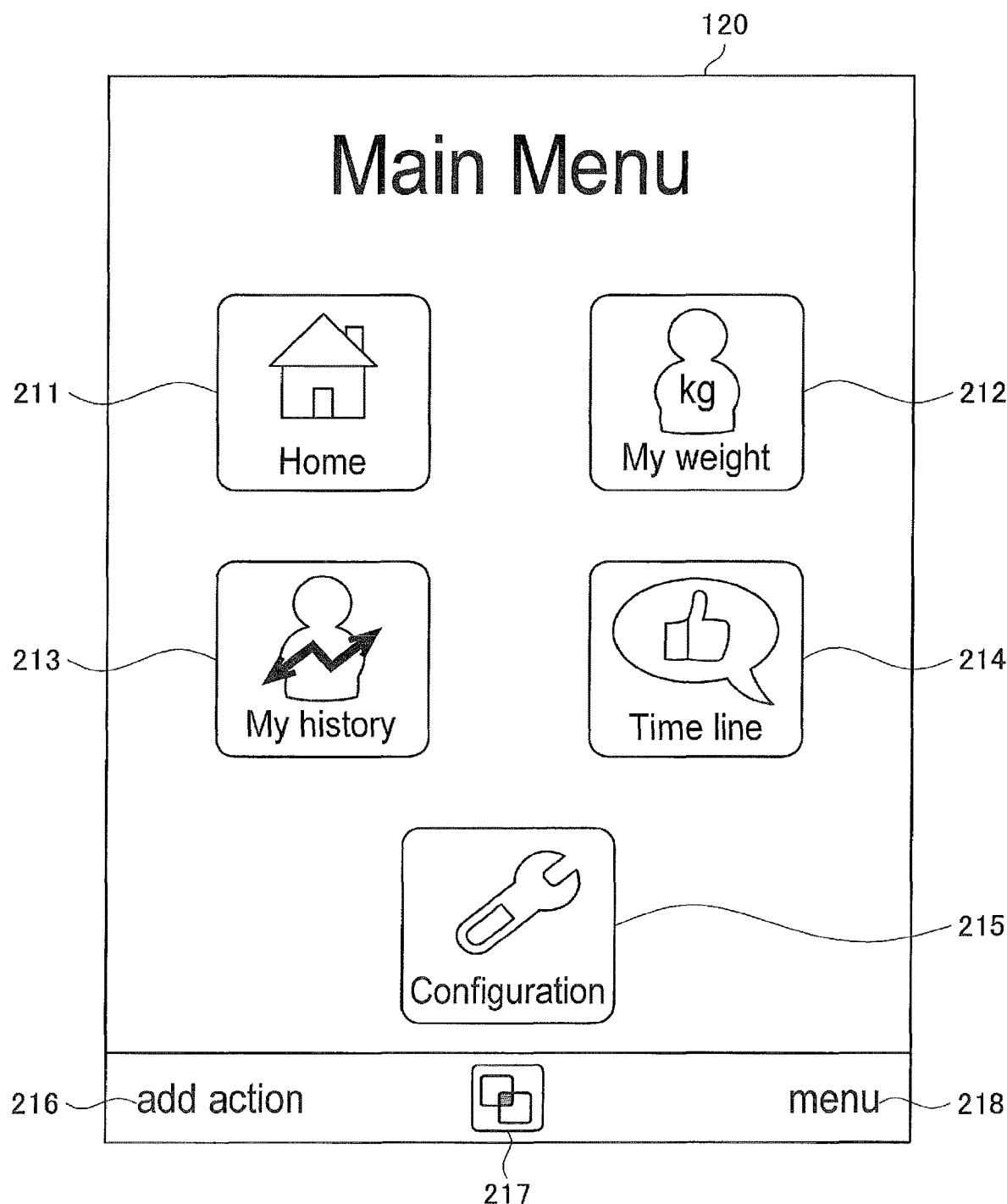
FIG. 6 is an explanatory diagram which shows an example of information displayed on a display section 120.

FIG. 6 is an explanatory diagram which shows an example of information displayed on the display section 120 of the portable terminal 100. The explanatory diagram shown in FIG. 6 is an example of a main menu screen displayed on the display section 120 by transiting from the login screen of FIG. 5, in the case where the login process by the diet support application installed in the portable terminal 100 is successful.

A button 211 for transiting to the home screen for registering actions related to the diet, a button 212 for transiting to a weight registration screen for inputting the present weight of the user, a button 213 for transiting to a history screen which displays an action history and changes in the weight of the user, a button 214 for transiting to a timeline screen which displays actions registered by the user himself or herself and other users, and a button 215 for transiting to a setting screen, are displayed on the main menu screen of the diet support application shown in FIG. 6.

Further, a label 216 for transiting to a screen for adding actions executed by the user for the diet to the home screen, which will be described later, a label 218 for transiting to the main menu screen shown in FIG. 6, and an icon 217 for transiting to the home screen, which will be described later, are displayed on the main menu screen of the diet support application shown in FIG. 6. The diet support application may display the labels 216, 218 and the icon 217 on any of the screens.

Figure 7:
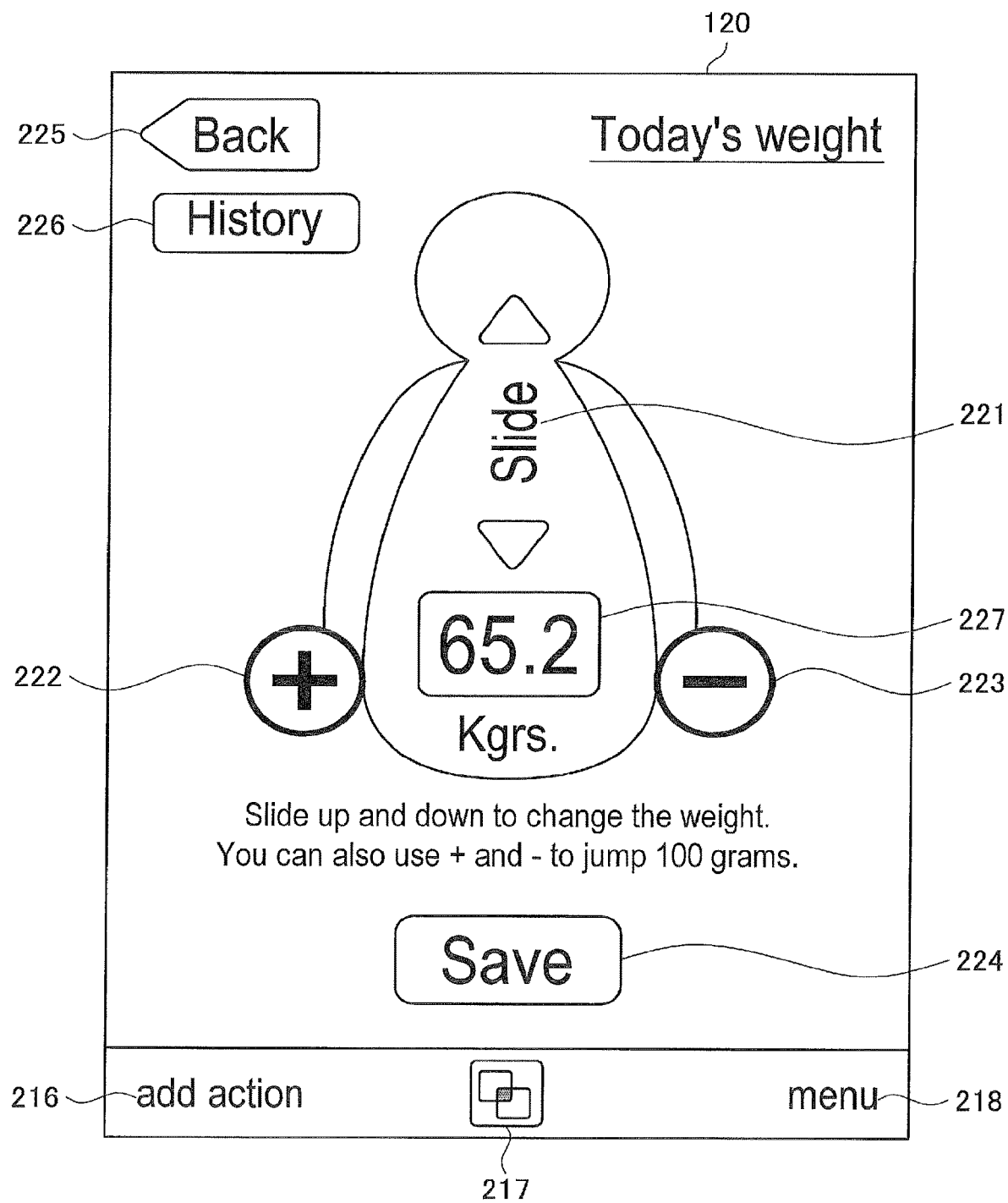
FIG. 7 is an explanatory diagram which shows an example of information displayed on a display section 120.

FIG. 7 is an explanatory diagram which shows an example of information displayed on the display section 120 of the portable terminal 100. The explanatory diagram shown in FIG. 7 is an example of a weight registration screen displayed on the display section 120 by transiting from the main menu screen shown in FIG. 6, in the case where the button 212 is selected by the user of the portable terminal 100 on the main menu screen shown in FIG. 6.

A slide part 221 for inputting a weight, buttons 222 and 223 for finely adjusting the weight input by the user using the slide part 221, and a button 224 for saving the input weight, are displayed on the weight registration screen of the diet support application shown in FIG. 7. Further, a button 225 for returning to the main menu screen shown in FIG. 6, a button 226 for transiting to the weight history screen which displays changes in the weight of the user, and a weight display part 227 in which the value input by the user is displayed, are displayed on the weight registration screen of the diet support application shown in FIG. 7.

The slide part 221 has a function which allows the user to input a weight by sliding up and down with a finger. The diet support application operates so that the value of the weight displayed in the weight display part 227 increases when the user slides the slide part 221 in an upwards direction with a finger, and conversely the value of the weight displayed in the weight display part 227 decreases when the user slides the slide part 221 in a downwards direction. By having the slide part 221, the diet support application is capable of inputting an intuitive weight for the user.

The buttons 222 and 223 have a function which finely adjusts the weight input by the user by using the slide part 221. While the input of the weight using the slide part 221 has an intuitive operation, it is not suitable for detailed changes of the value. Accordingly, the diet support application includes the buttons 222 and 223. The button 222 has a function which increases the value of the weight displayed in the weight display part 227 by 100 grams at a time, and the button 223 has a function which decreases the value of the weight displayed in the weight display part 227 by 100 grams at a time. The weight input by the operations for the slide part 221 and the buttons 222 and 223 by the user is saved in the diet support application by the selection of the button 224 by the user.

Figure 8:
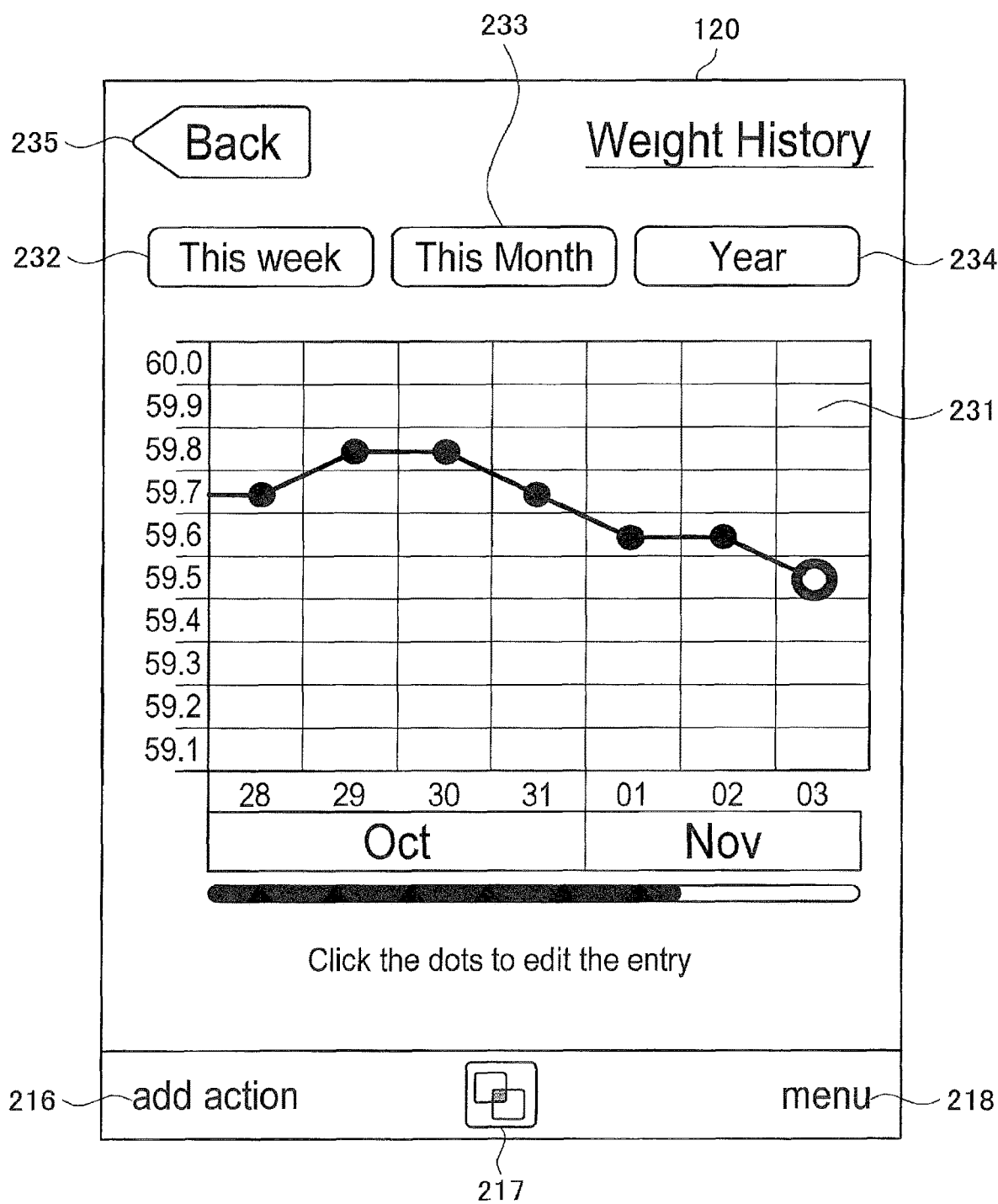
FIG. 8 is an explanatory diagram which shows an example of information displayed on a display section 120.

FIG. 8 is an explanatory diagram which shows an example of information displayed on the display section 120 of the portable terminal 100. The explanatory diagram shown in FIG. 8 is an example of a weight history screen displayed on the display section 120 by transiting from the weight registration screen shown in FIG. 7, in the case where the button 226 is selected by the user of the portable terminal 100 on the weight registration screen shown in FIG. 7.

A weight change display part 231 which shows changes in the weight of the user by a graph, buttons 232, 233 and 234 for changing the display range of the horizontal axis of the graph, and a button 235 for returning to the weight registration screen shown in FIG. 7, are displayed on the weight history screen of the diet support application shown in FIG. 8.

The weight change display part 231 shows changes in the weight of the user by a graph by setting the horizontal axis as time and the vertical axis as weight. While changes in the weight of the user are shown in FIG. 8 by a graph in the weight change display part 231 in units of days, the diet support application can change the units of the horizontal axis of the graph by allowing the user to select the buttons 232, 233 and 234.

For example, when the user selects the button 232, the diet support application changes the display range of the horizontal axis of the graph shown in the weight change display part 231 to a range of one week. Similarly, when the user selects the button 233, the diet support application changes the display range of the horizontal axis of the graph shown in the weight change display part 231 to a range of one month, and when the button 234 is selected, the diet support application changes the display range to a range of one year.

Note that, in the example shown in FIG. 8, while the diet support application changes the display range of the horizontal axis of the graph shown in the weight change display part 231 by the selection of the buttons 232, 233 and 234, it is not limited to such an example. For example, the diet support application may change the display range of the horizontal axis of the graph shown in the weight change display part 231, in accordance with a slide operation performed for the weight change display part 231 by an operation of the operation section 130 by the user.

Figure 9:
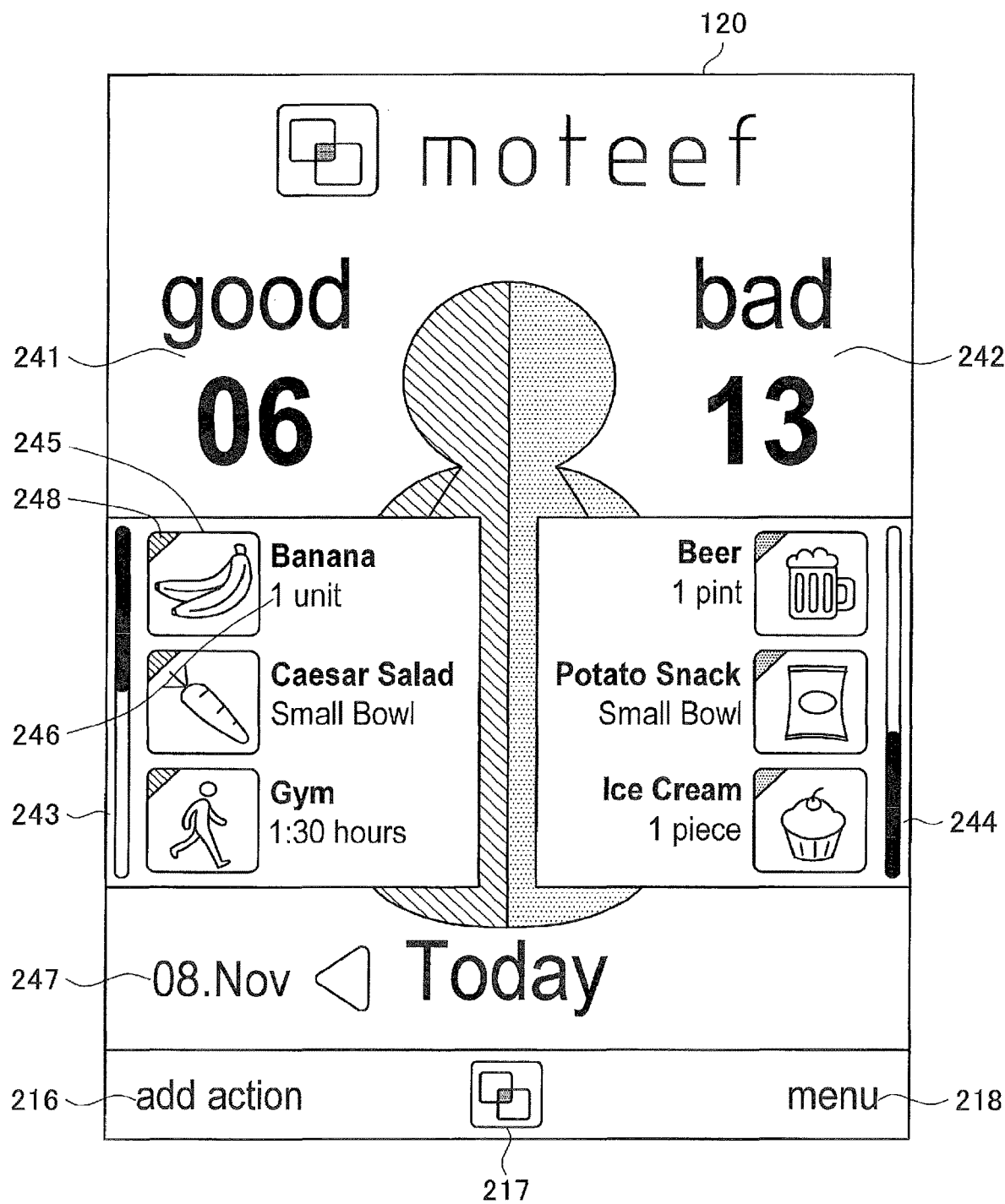
FIG. 9 is an explanatory diagram which shows an example of information displayed on a display section 120.

FIG. 9 is an explanatory diagram which shows an example of information displayed on the display section 120 of the portable terminal 100. The explanatory diagram shown in FIG. 9 is an example of a home screen of the diet support application displayed on the display section 120 by transiting from the main menu screen shown in FIG. 6, in the case where the button 211 is selected by the user of the portable terminal 100 on the main menu screen of the diet support application shown in FIG. 7.

A region 241 which shows the number of positive (good) actions which have been set for the diet, and a region 242 which shows the number of negative (bad) actions which have been set for the diet, are displayed on the home screen of the diet support application shown in FIG. 9. Further, a region 243 which displays icons indicating positive actions for the diet, and a region 244 which displays icons indicating negative actions for the diet, are displayed on the home screen shown in FIG. 9.

Further, icons 245 indicating positive actions for the diet, and icon description parts 246 which show a description of these icons, are displayed in the region 243 of the home screen of the diet support application shown in FIG. 9.

The diet support application changes the numbers displayed in the region 241 or the region 242, by having the user select an icon displayed in the region 243 or the region 244, and registering that an action corresponding to this icon has been executed. For example, when the user selects an icon 245 and registers on the check in screen, which will be described later, that an action corresponding to this icon has been performed, the diet support application increases the value displayed in the region 241 by one. Conversely, when the user selects an icon displayed in the region 244 and registers on the check in screen that an action corresponding to this icon has been performed, the diet support application increases the value displayed in the region 242 by one.

A type display part 248, which shows whether an action corresponding to this icon is a positive action or a negative action for the diet, is included on the upper left portion of the icon 245 shown in FIG. 9. For example, if the action is a positive action for the diet, a blue type display part 248 is superimposed on the icon 245, and if the action is a negative action, a red type display part 248 is superimposed on the icon 245.

For example, walking, running, other sports and eating meals with few calories are positive actions for the diet. Further, eating meals with high calories, drinking alcohol and smoking are negative actions for the diet. The diet support application may prepare icons corresponding to such actions in advance and display the prepared icons on the home screen.

Further, for example, while the diet support application is set so as to be added to the home screen by the user himself or herself, the diet support application may be created by other users, and high evaluations or the like from other users may be displayed on the home screen.

Note that, in the example shown in FIG. 9, while the type display part 248 is included in the upper left portion of each icon 245, the present disclosure is not limited to such an example. For example, the type display part 248 may be included in the form of a frame surrounding each icon 245.

A date change section 247 for changing a target date on which the user performs an action is also shown on the home screen shown in FIG. 9. By selecting the date change section 247 by an operation of the operation section 130 by the user, the diet support application can change a target date on which the user performs an action.

The diet support application may change the icons displayed on the home screen in accordance with a time zone. For example, if the time at which the diet support application is to be used is during the morning, the diet support application displays icons suitable for actions during the morning, and may remove icons from a display target which are unsuitable for actions during the morning.

Further, when the user continuously registers the same action over several days, the diet support application may change the icon corresponding to this action, or may change the display for the range of the icon.

Figure 10:
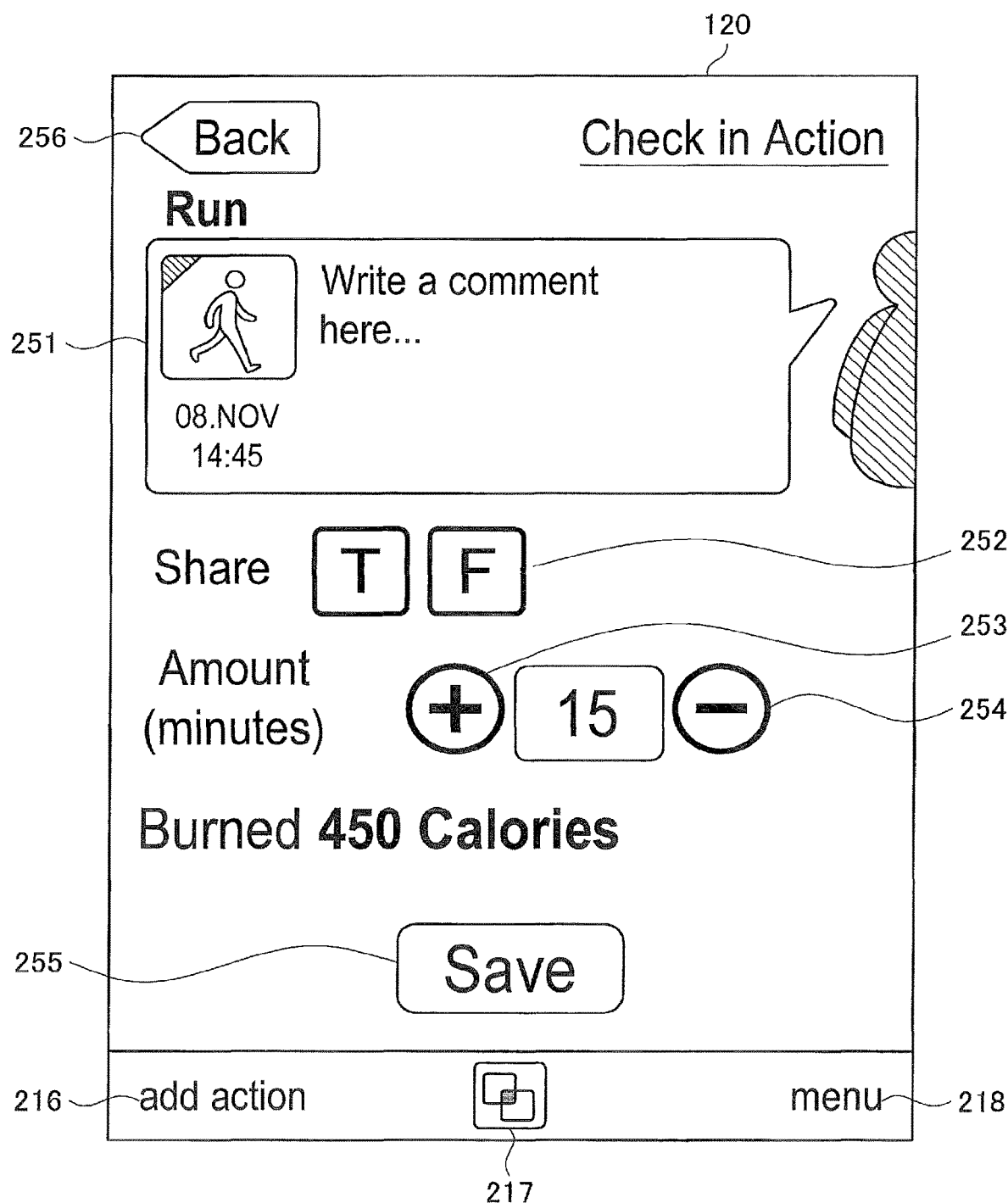
FIG. 10 is an explanatory diagram which shows an example of information displayed on a display section 120.

FIG. 10 is an explanatory diagram which shows an example of information displayed on the display section 120 of the portable terminal 100. The explanatory diagram shown in FIG. 10 is an example of a check in screen of the diet support application displayed on the display section 120 by transiting from the home screen shown in FIG. 9, in the case where one of the icons 245 is selected by the user of the portable terminal 100 on the home screen of the diet support application shown in FIG. 9. The check in screen shown in FIG. 10 is an example of a case where the action corresponding to the icon selected by the user is running.

A comment input column 251 for allowing the user to input a comment for the action corresponding to the icon selected by the user, and buttons 252 for sharing the action corresponding to the icon selected by the user by a Web service such as another SNS, are shown on the check in screen of the diet support application shown in FIG. 10. Further, buttons 253 and 254 which increase and decrease the amount of the action corresponding to the icon selected by the user, and a button 255 which saves the action corresponding to the icon selected by the user in the diet support application, are shown on the check in screen of the diet support application shown in FIG. 10. Further, a button 256 for returning to the home screen of the diet support application shown in FIG. 9 is also shown on the check in screen of the diet support application shown in FIG. 10.

By selecting the buttons 253 and 254 by operating the operation section 130, the user of the portable terminal 100 can increase or decrease the amount of the action corresponding to the icon selected by the user. For example, since the action corresponding to the icon selected by the user is running on the check in screen shown in FIG. 10, the user of the portable terminal 100 can increase or decrease the time of running, by selecting the buttons 253 and 254. Also, by selecting the button 255 by operating the operation section 130, the user of the portable terminal 100 can save, to the server apparatus 10, that running has been performed, via the diet support application.

The diet support application can allow the user of the portable terminal 100 to enter a comment for the action corresponding to the icon selected by the user in the comment input column 251. Since the action corresponding to the icon selected by the user is running on the check in screen shown in FIG. 10, the user of the portable terminal 100 can enter a feeling from running in the comment input column 251. The contents input in the comment input column 251 are saved in the server apparatus 10, via the diet support application by the selection of the button 255.

Note that if the contents of the action performed by the user are to remain as history in the server apparatus 10, there is the possibility that the information is not wanted to be shared with other users. By considering such a case, the diet support application may have a function which selects, at the time when saving an action performed by the user, whether or not to share this action with other users.

In the present embodiment, while a user registers an action by the check in screen such as shown in FIG. 10, the present disclosure is not limited to such an example. For example, for an icon displayed on the home screen such as shown in FIG. 9, the diet support application may register that an action corresponding to this icon has been performed, by detecting an operation different to the operation which transitions to the check in screen. For example, if the operation which transitions to the check in screen is a tap operation of an icon, the diet support application may register that an action corresponding to this icon has been performed, by detecting a long push operation of the icon.

Further, for example, by the detection of a long push operation of an icon on the home screen such as shown in FIG. 9, the diet support application may display numerals in which the values change by the operation of the buttons 253 and 254 on the check in screen of FIG. 10. Further, for example, by the frequency of a tap operation of an icon on the home screen such as shown in FIG. 9, the diet support application may register the frequency at which an action corresponding to the icon is performed.

In this way, by allowing the user to register an action on the home screen such as shown in FIG. 9 or on the check in screen such as shown in FIG. 10, the diet support application operated by the portable terminal 100 can acquire a selection condition of the icon corresponding to this action. The diet support application can generate information for sharing this action with other users, from the selection condition of the acquired icon. An example of information for sharing this action with other users is shown hereinafter.

Figure 11:
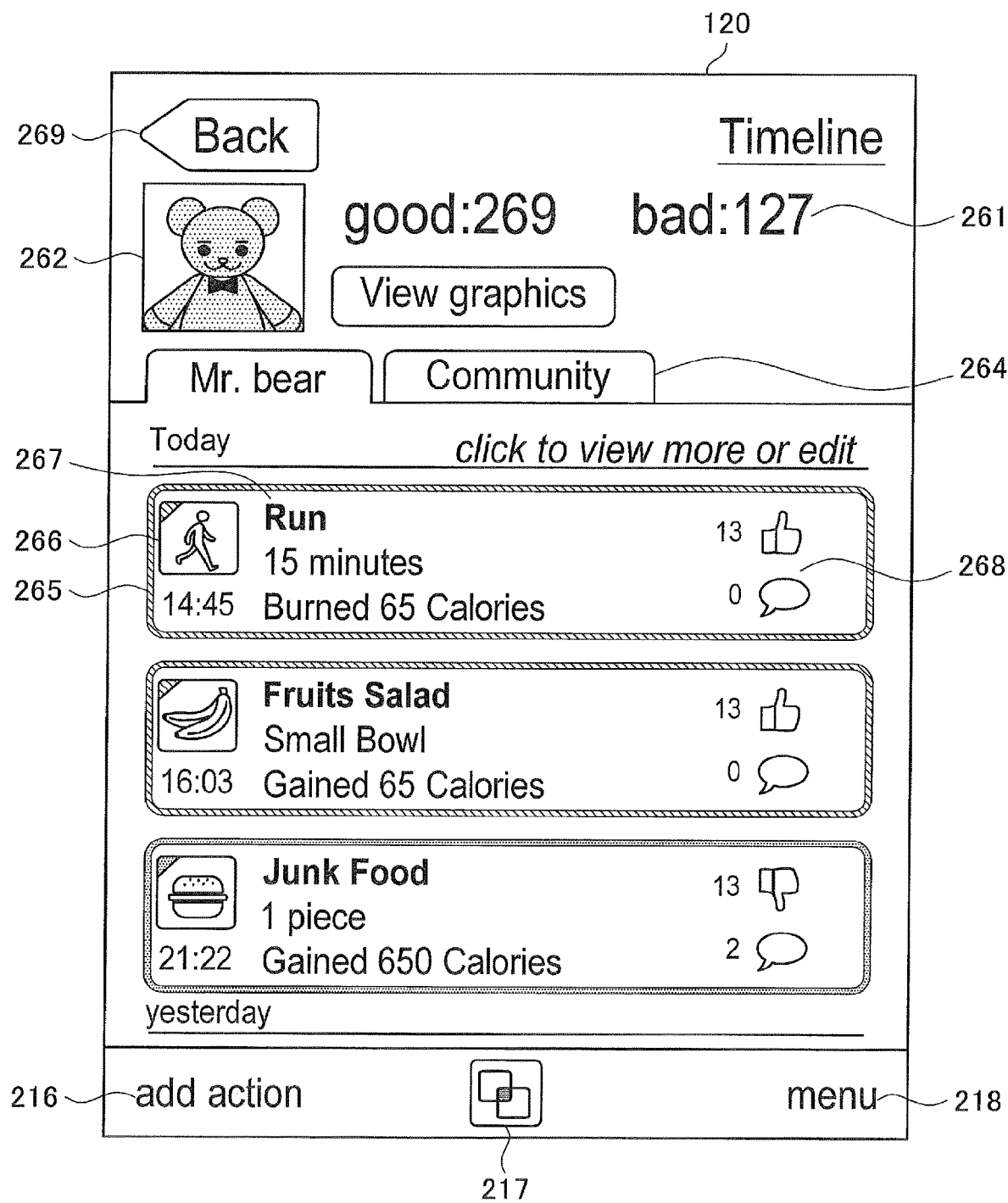
FIG. 11 is an explanatory diagram which shows an example of information displayed on a display section 120.

FIG. 11 is an explanatory diagram which shows an example of information displayed on the display section 120 of the portable terminal 100. The explanatory diagram shown in FIG. 11 is an example of a timeline screen of the diet support application displayed on the display section 120 by transiting from the main menu screen shown in FIG. 6, in the case where the button 214 is selected by the user of the portable terminal 100 on the main menu screen of the diet support application shown in FIG. 6.

The timeline screen of the diet support application shown in FIG. 11 is a screen for displaying, in a time series, actions which the user himself or herself has registered on the check in screen shown in FIG. 10 and saved in the server apparatus 10. A region 261 which shows the number of positive actions and negative actions which have been set for the diet by the user himself or herself, and a profile image 262 of the user himself or herself, are displayed on the timeline screen of the diet support application shown in FIG. 11. Further, a tab 263 for displaying, in a time series, a history of the actions of the user himself or herself, and a tab 264 for displaying, in a time series, a history of the actions included from other users, are displayed on the timeline screen of the diet support application shown in FIG. 11.

Further, regions 265 which show the details of actions registered by the user are displayed for each of these actions on the timeline screen of the diet support application shown in FIG. 11. Icons 266 corresponding to the actions registered by the user, detailed information 267 of the actions registered by the user, and evaluation information 268 which shows the amount of evaluations or the amount of comments from other users for this action, are displayed in the region 265. Further, a button 269 for returning to the main menu screen of the diet support application shown in FIG. 6 is also displayed on the timeline screen of the diet support application shown in FIG. 11.

By viewing the timeline screen of the diet support application shown in FIG. 11, the user of the portable terminal 100 can confirm when and what kind of actions have been performed by the user himself or herself for the diet, or what kinds of evaluations are given by other users for this action. In particular, by confirming what kinds of evaluations are given by other users for the actions performed by the user himself or herself for the diet, the user of the portable terminal 100 can highly expect to maintain or improve motivation for the diet.

That is, a high evaluation for an action performed for the diet by the user himself or herself can be highly expected to be connected to maintaining or improving motivation for the diet of this user, by continuously executing this action.

The diet support application can display not only actions registered by the user himself or herself on the timeline screen, but also actions registered by other users connected to the user himself or herself.

Figure 12:
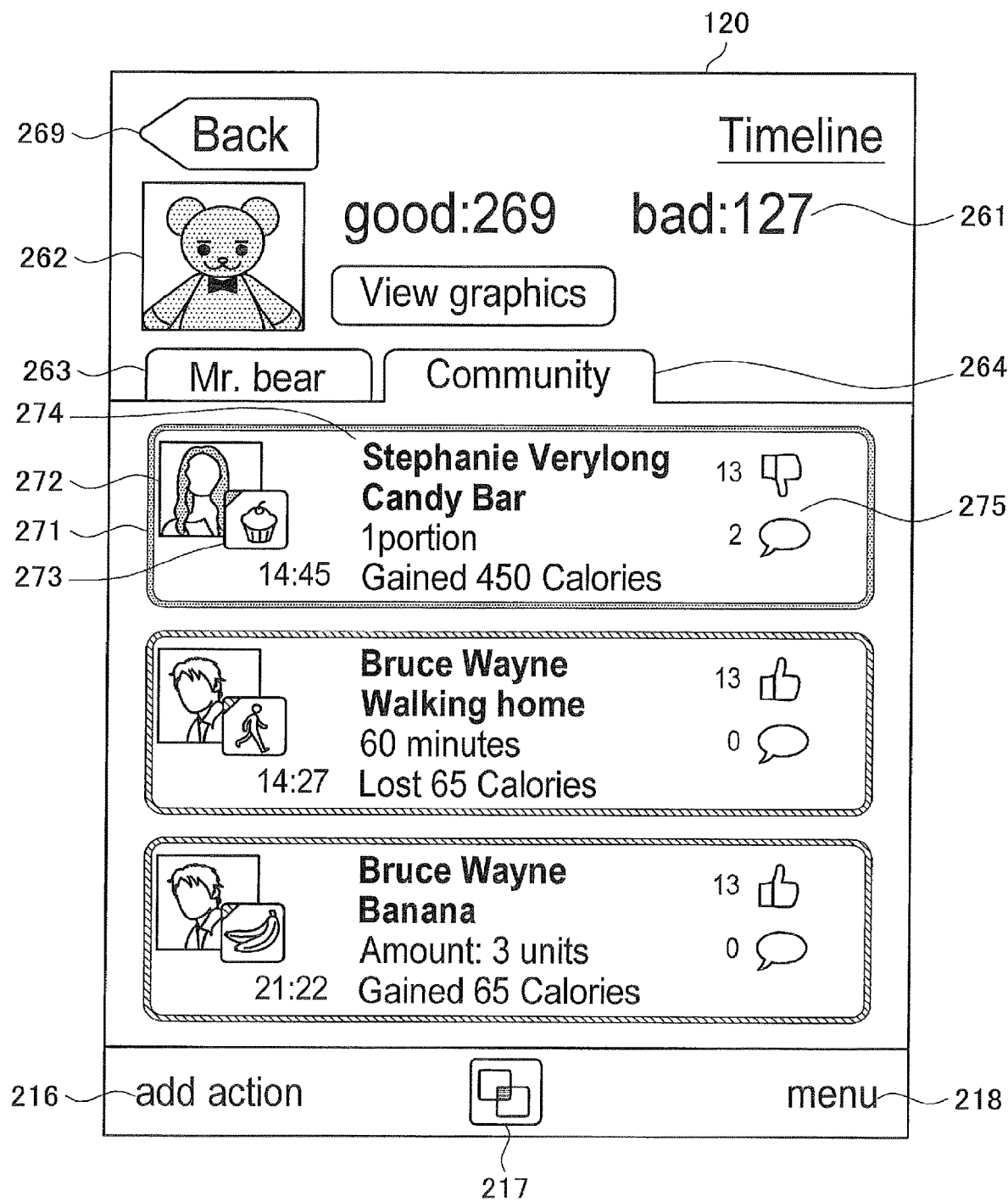
FIG. 12 is an explanatory diagram which shows an example of information displayed on a display section 120.

FIG. 12 is an explanatory diagram which shows an example of information displayed on the display section 120 of the portable terminal 100. The explanatory diagram shown in FIG. 12 is an example of a timeline screen of the diet support application displayed on the display section 120 by transiting from the timeline screen shown in FIG. 11, in the case where the tab 264 is selected by the user of the portable terminal 100 on the timeline screen of the diet support application shown in FIG. 11.

Regions 271 which display details of actions registered by other users are displayed for each of these actions on the timeline screen of the diet support application shown in FIG. 12. A profile image 272 of the user registering an action, an icon 273 corresponding to the action registered by the user, detailed information 274 of the action registered by the user, and evaluation information 275 which shows the amount of evaluations or the amount of comments from other users for this action, are displayed in the region 271.

By viewing the timeline screen of the diet support application shown in FIG. 12, the user of the portable terminal 100 can confirm when and what kind of actions have been performed by other users for the diet, or what kinds of evaluations are given by other users for this action. In particular, by confirming what kinds of evaluations are given by other users for actions performed for the diet, the user of the portable terminal 100 can highly expect to maintain or improve motivation for the diet.

That is, a high evaluation for an action performed for the diet by other users can be highly expected to be connected to maintaining or improving motivation for the diet of the user himself or herself, by having the user himself or herself add this action if not already performed.

The diet support application can transition to a screen which displays the details of each action, from the timeline screen shown in FIG. 12, by an operation of the user of the portable terminal 100.

Figure 13:
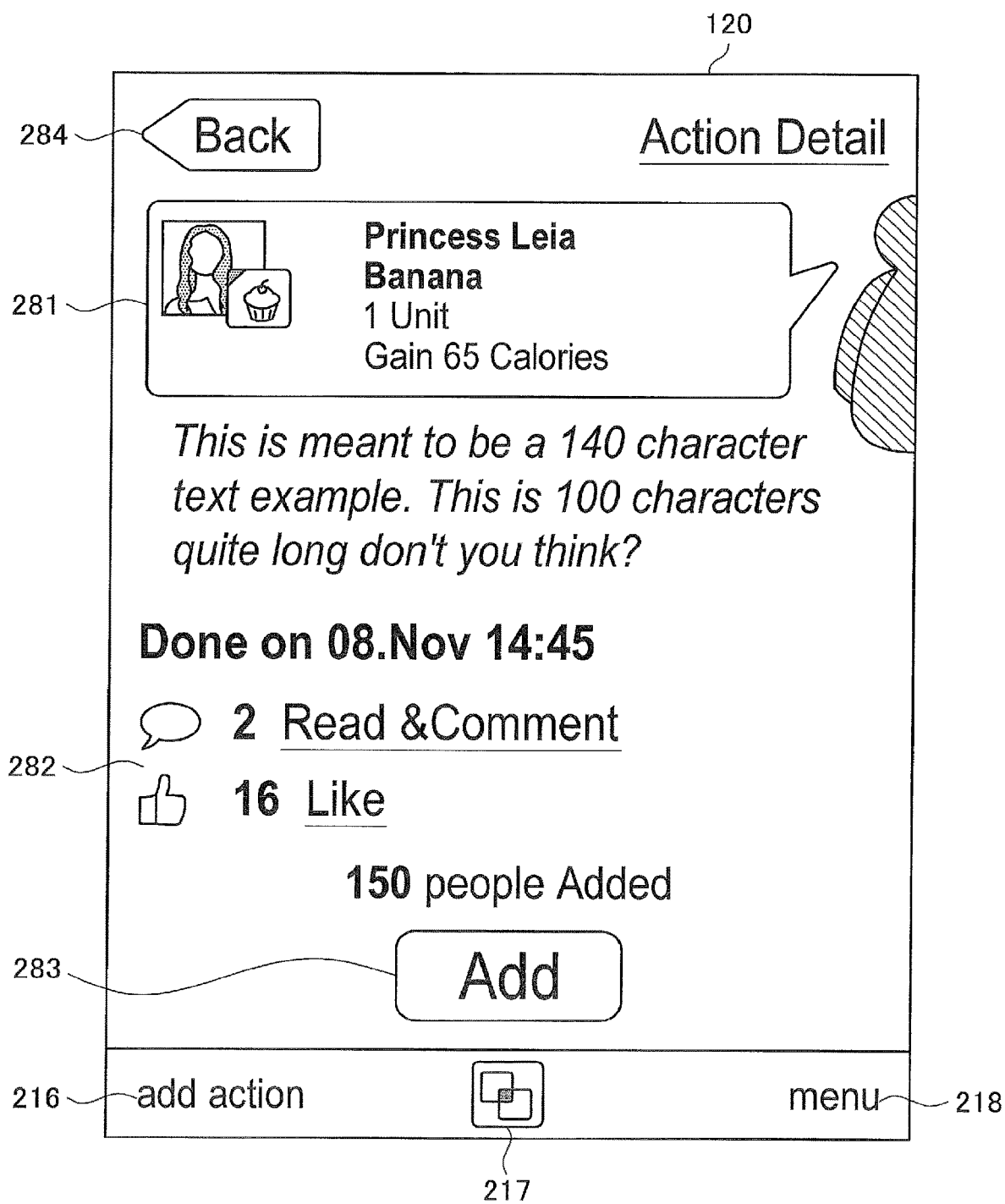
FIG. 13 is an explanatory diagram which shows an example of information displayed on a display section 120.

FIG. 13 is an explanatory diagram which shows an example of information displayed on the display section 120 of the portable terminal 100. The explanatory diagram shown in FIG. 13 is an example of an action detail screen of the diet support application displayed on the display section 120 by transiting from the timeline screen shown in FIG. 12, in the case where the region 271 is selected by the user of the portable terminal 100 on the timeline screen of the diet support application shown in FIG. 12.

A region 281 which shows the details of the action selected by the user of the portable terminal 100, and evaluation information 282 which shows the amount of evaluations or the amount of comments from other users for this action, are displayed on the action detail screen of the diet support application shown in FIG. 13. Further, a button 283 for adding the displayed action as an action of the user himself or herself, and a button 284 for returning to the timeline screen shown in FIG. 12, are displayed on the action detail screen of the diet support application shown in FIG. 13.

In the case where the action of other users displayed on the action detail screen of the diet support application is added as an action for the diet of the user himself or herself, the user of the portable terminal 100 selects the button 283 by operating the operation section 130. The action added by the selection of the button 283 is displayed on the home screen of the diet support application shown in FIG. 9.

Further, the diet support application can allow the user of the portable terminal 100 to evaluate the action of other users displayed on the action detail screen, and can attach a comment for this action.

Figure 14:
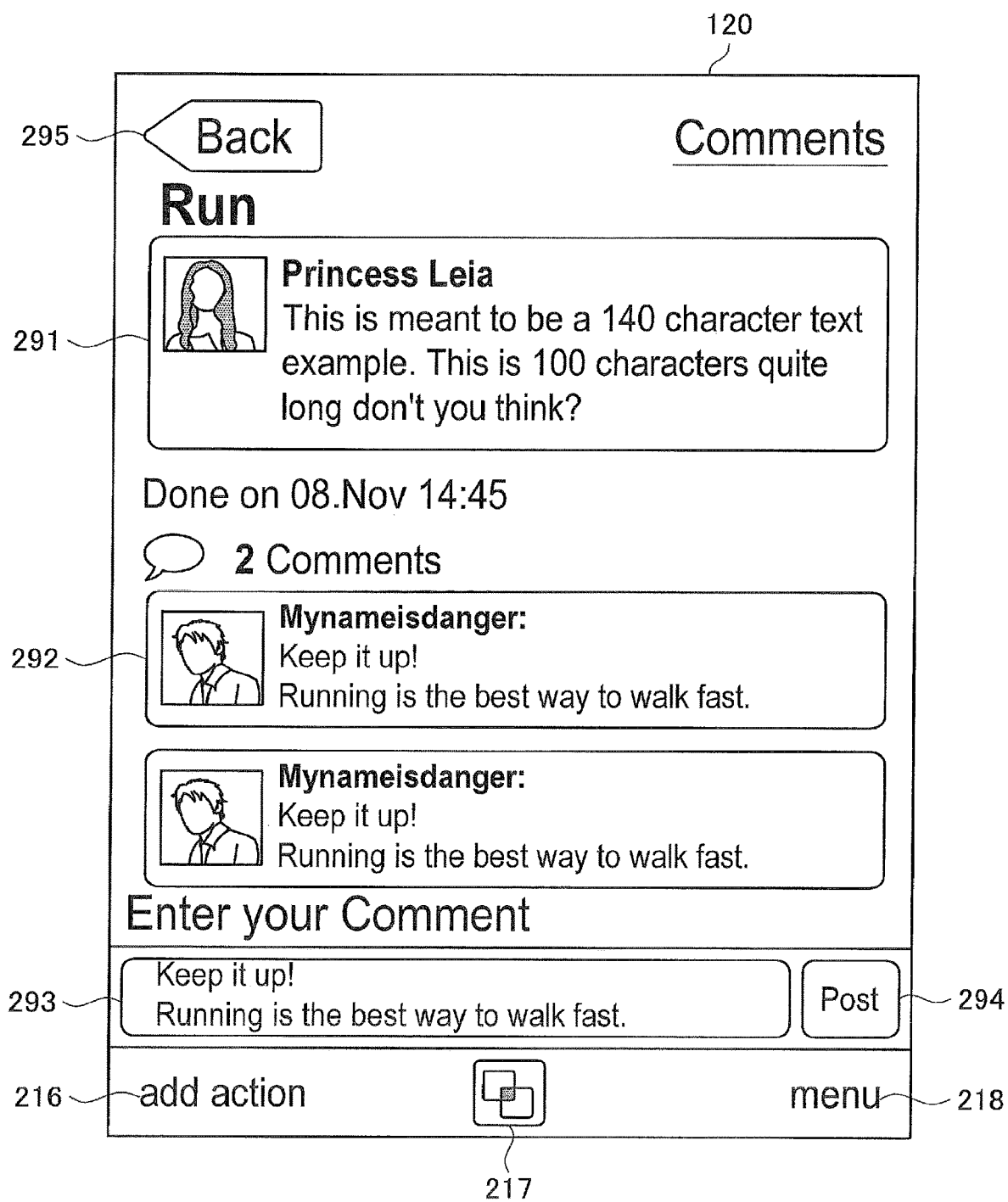
FIG. 14 is an explanatory diagram which shows an example of information displayed on a display section 120.

FIG. 14 is an explanatory diagram which shows an example of information displayed on the display section 120 of the portable terminal 100. The explanatory diagram shown in FIG. 14 is an example of a comment input screen of the diet support application displayed on the display section 120 by transiting from the action detail screen of the diet support application shown in FIG. 13, in the case where the evaluation information 282 is selected by the user on the action detail screen of the diet support application shown in FIG. 13.

A region 291 which shows the details of the action selected by the user of the portable terminal 100, and regions 292 which display comments attached to this action, are displayed on the comment input screen of the diet support application shown in FIG. 14. Further, a region 293 for inputting a comment for the action selected by the user of the portable terminal 100, and a button 294 for contributing the comment input in the region 293, are displayed on the comment input screen of the diet support application shown in FIG. 14. Further, a button 295 for returning to the action detail screen of the diet support application shown in FIG. 13 is displayed on the comment input screen of the diet support application shown in FIG. 14.

The diet support application can allow the user of the portable terminal 100 to input a comment, by the comment input screen such as shown in FIG. 14. When the user of the portable terminal 100 inputs a comment in the region 293 by operating the operation section 130, and selects the button 294, the diet support application saves the comment input in the region 293 in the server apparatus 10. In this way, by including a function which allows a comment to be input for actions registered by each user, the diet support application can highly expect to maintain or improve motivation for the diet of each user.

In order to enable an action, which is not present on the home screen of the diet support application shown in FIG. 9, to be registered on the check in screen by the user of the portable terminal 100, the diet support application has a function which allows the user of the portable terminal 100 to search for whether or not this action is registered by other users.

Figure 15:
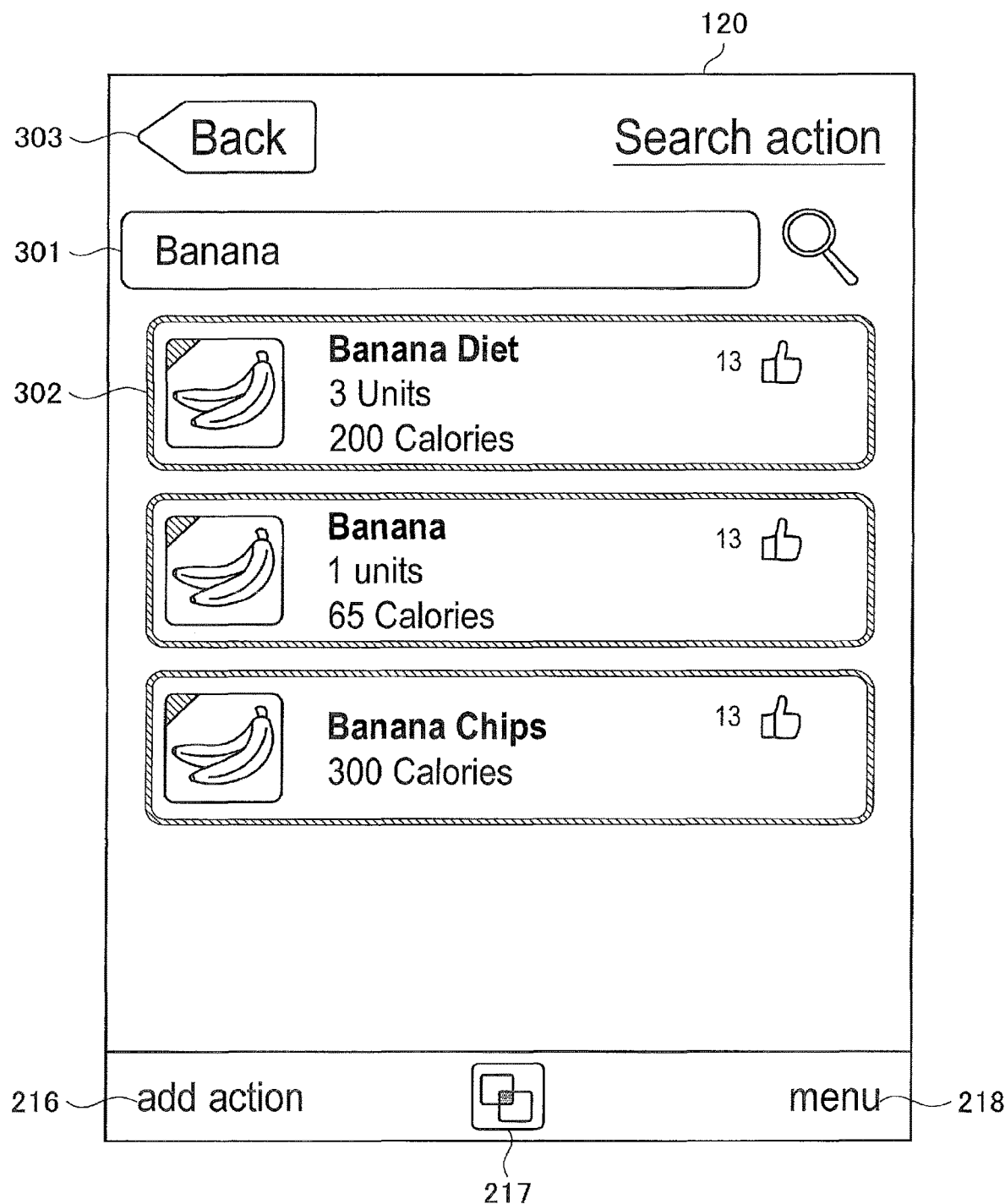
FIG. 15 is an explanatory diagram which shows an example of information displayed on a display section 120.

FIG. 15 is an explanatory diagram which shows an example of information displayed on the display section 120 of the portable terminal 100. The explanatory diagram shown in FIG. 15 is an example of a search screen of the diet support application displayed on the display section 120 by transiting from the home screen of the diet support application shown in FIG. 9, in the case where the label 216 is selected by the user, for example, on the home screen of the diet support application shown in FIG. 9.

A region 301 for allowing the user of the portable terminal 100 to input a search condition, and regions 302 in which actions registered in the server apparatus are displayed which match the search condition input in the region 301, are displayed on the search screen of the diet support application shown in FIG. 15. Further, a button 303 for returning to the screen prior to the transition is also displayed on the search screen of the diet support application shown in FIG. 15.

By displaying the search screen such as shown in FIG. 15, the diet support application can indicate actions related to the diet for the user of the portable terminal 100, which match the search condition and which are registered in the server apparatus 10.

When an action displayed in the region 302 of the search screen shown in FIG. 15 is selected by the user of the portable terminal 100, the diet support application transitions to a screen for adding this action to the home screen.

Figure 16:
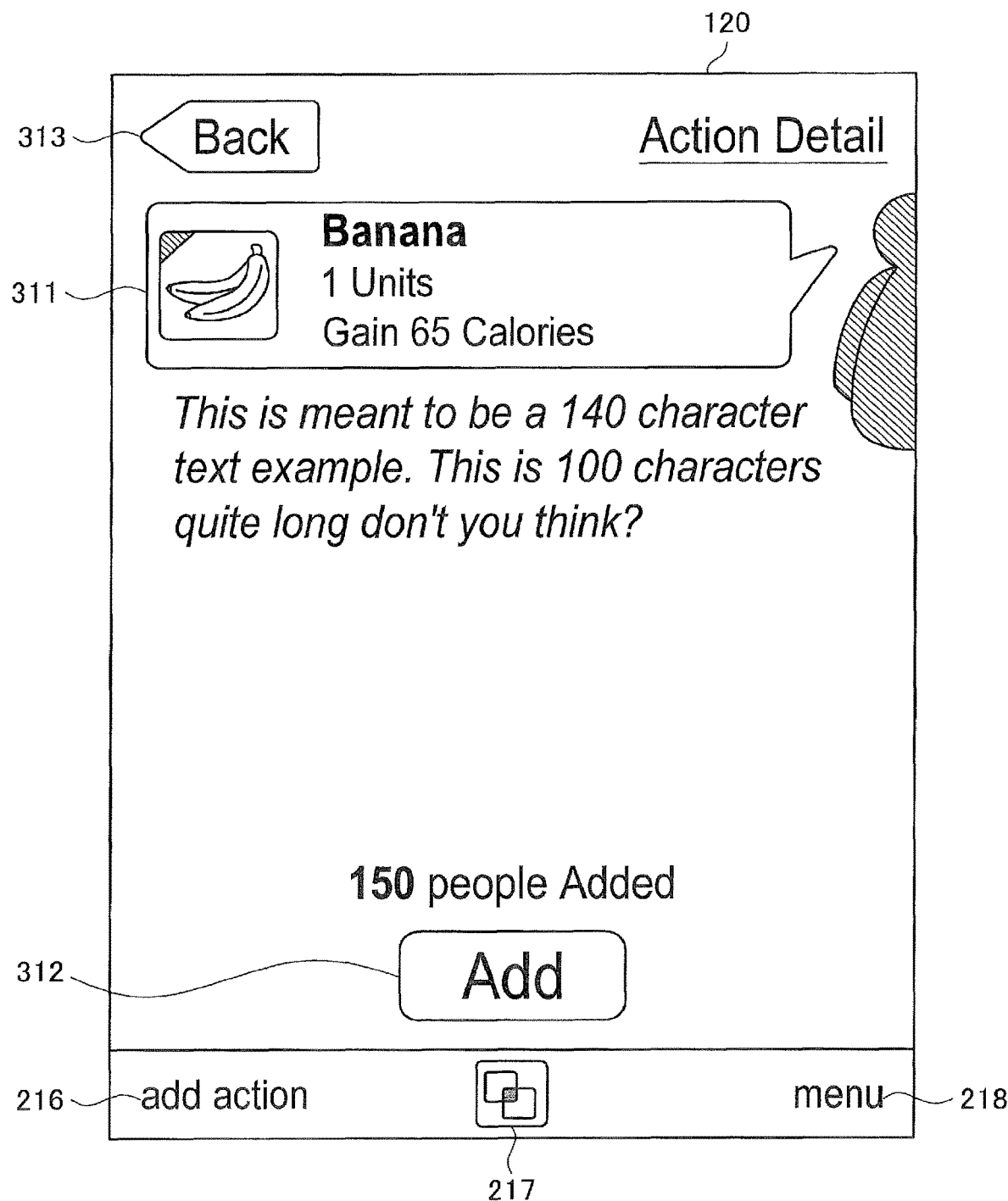
FIG. 16 is an explanatory diagram which shows an example of information displayed on a display section 120.

FIG. 16 is an explanatory diagram which shows an example of information displayed on the display section 120 of the portable terminal 100. The explanatory diagram shown in FIG. 16 is an example of an action addition screen of the diet support application displayed on the display section 120 by transiting from the search screen of the diet support application shown in FIG. 15, in the case where an action is selected by the user on the search screen of the diet support application shown in FIG. 15.

A region 311 which displays the details of the action selected by the user of the portable terminal 100 on the search screen, and a button 312 for adding the action selected by the user of the portable terminal 100 on the search screen to the home screen, are displayed on the action addition screen of the diet support application shown in FIG. 16. Further, a button 313 for returning to the search screen is also displayed on the action addition screen of the diet support application shown in FIG. 16.

By viewing the action addition screen of the diet support application such as that of FIG. 16, and if the action is considered to be suitable for the user himself or herself, selecting the button 312 by operating the operation section 130, the user of the portable terminal 100 can add the action displayed on the action addition screen to the home screen. For example, in the example shown in FIG. 16, 150 people have registered on the home screen eating a banana, and if it is judged that eating a banana is also connected to the diet for the user himself or herself, the user of the portable terminal 100 can add, to the home screen, the action of eating a banana displayed on the action addition screen of FIG. 16, by selecting the button 312.

While up to here an example has been shown in the case where there are matching results in the server apparatus 10 for the search condition input by the user of the portable terminal 100, an example will be shown next in the case where there are no matching results in the server apparatus 10 for the search condition input by the user of the portable terminal 100.

Figure 17:
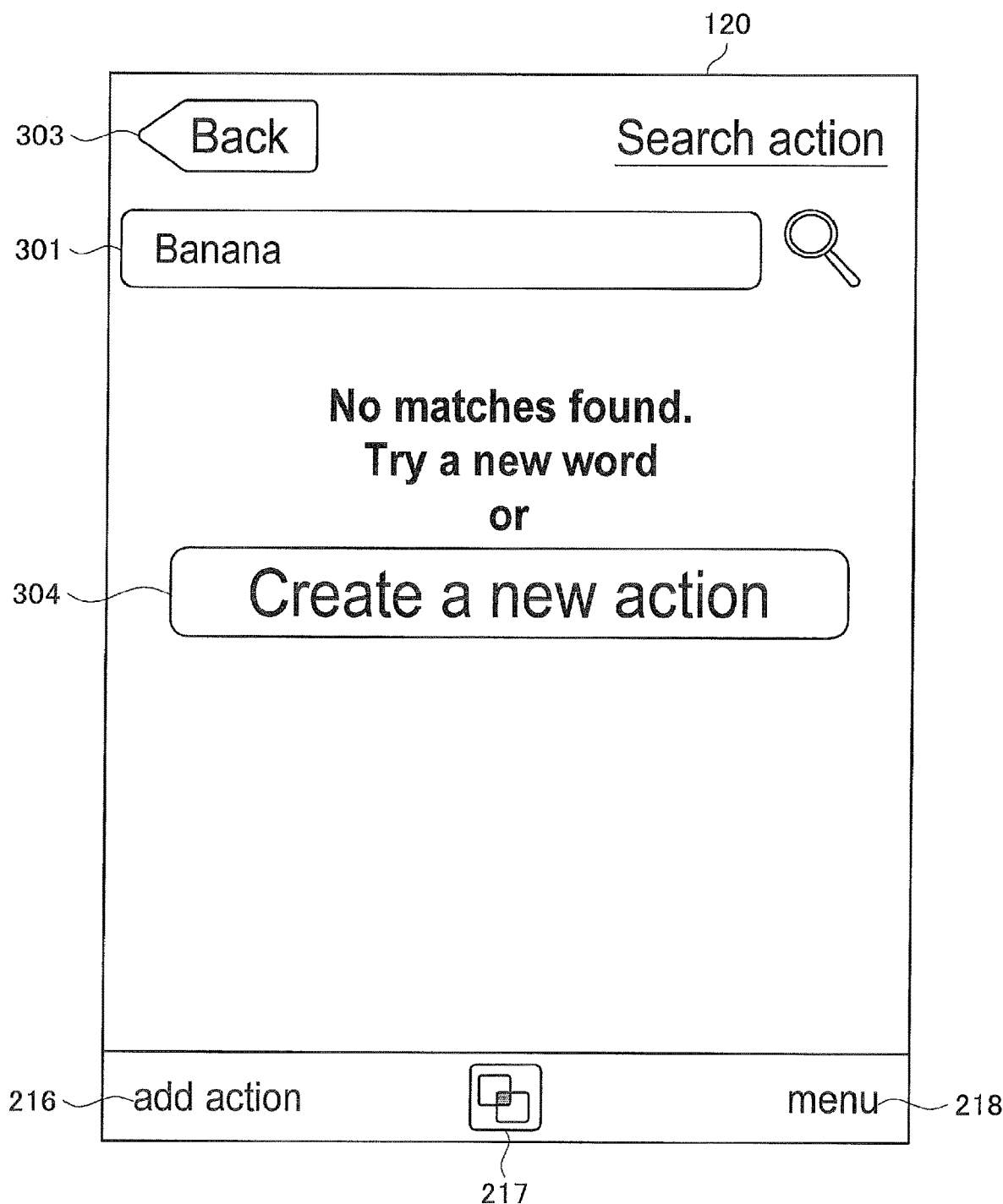
FIG. 17 is an explanatory diagram which shows an example of information displayed on a display section 120.

FIG. 17 is an explanatory diagram which shows an example of information displayed on the display section 120 of the portable terminal 100. The explanatory diagram shown in FIG. 17 is an example of a search screen of the diet support application, in the case where there are no matching results in the server apparatus 10 for the search condition input by the user of the portable terminal 100.

A message stating that there are no actions in the server apparatus 10 which match the search condition input in the region 301 is displayed on the search screen of the diet support application shown in FIG. 17. Also, in addition to the above described message, a button 304 for allowing the user of the portable terminal 100 to create a new action is displayed on the search screen of the diet support application shown in FIG. 17.

By allowing the user of the portable terminal 100 to select the button 304, the diet support application can create a new action related to the diet which does not exist in the server apparatus 10.

Figure 18:
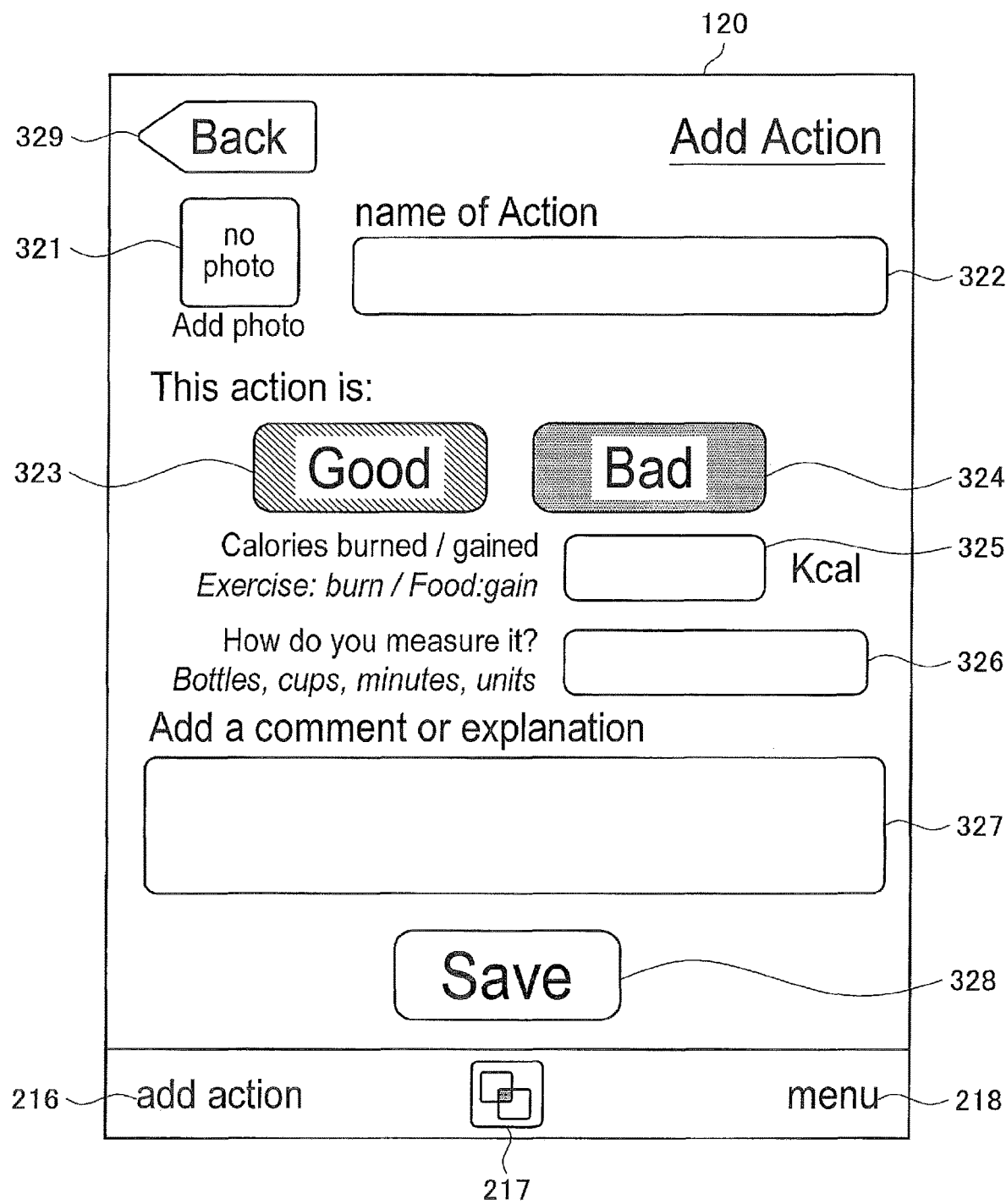
FIG. 18 is an explanatory diagram which shows an example of information displayed on a display section 120.

FIG. 18 is an explanatory diagram which shows an example of information displayed on the display section 120 of the portable terminal 100. The explanatory diagram shown in FIG. 18 is an example of an action addition screen of the diet support application displayed on the display section 120 by transiting from the search screen of the diet support application show in FIG. 17, in the case where the button 304 is selected by the user on the search screen of the diet support application shown in FIG. 17.

A region 321 in which an icon corresponding to the action is displayed, a region 322 in which the name of the action is input, a button 323 which indicates that this action is positive about the diet, and a button 324 which indicates that this action is negative about the diet, are displayed on the action addition screen of the diet support application shown in FIG. 18. Further, a region 325 for inputting to what extent calories are consumed by this action (or whether calories are acquired), and a region 326 for inputting the units of this action for one time, are displayed on the action addition screen of the diet support application shown in FIG. 18.

Further, a region 327 for inputting a comment for this action, a button 328 for saving the input contents, and a button 329 for returning to the search screen of the diet support application, are displayed on the action addition screen of the diet support application shown in FIG. 18.

The diet support application can allow the user of the portable terminal 100 to create a new action performed for the diet, by the action addition screen such as shown in FIG. 18. An icon related to the action may be created by the user himself or herself, or may be selected from among icons prepared by the diet support application in advance. For example, by allowing the user of the portable terminal 100 to select the region 321 by the operation section 130, the diet support application may transition from the action addition screen such as shown in FIG. 18 to a screen which specifies icons.

Note that, while items are shown in FIG. 18 which allows the user to set whether the action to be registered is positive or negative about the diet, the present disclosure is not limited to such an example. For example, at the time when the user registers that an action has been performed, the diet support application may allow the user to register whether the action is positive or negative about the diet.

Figure 19:
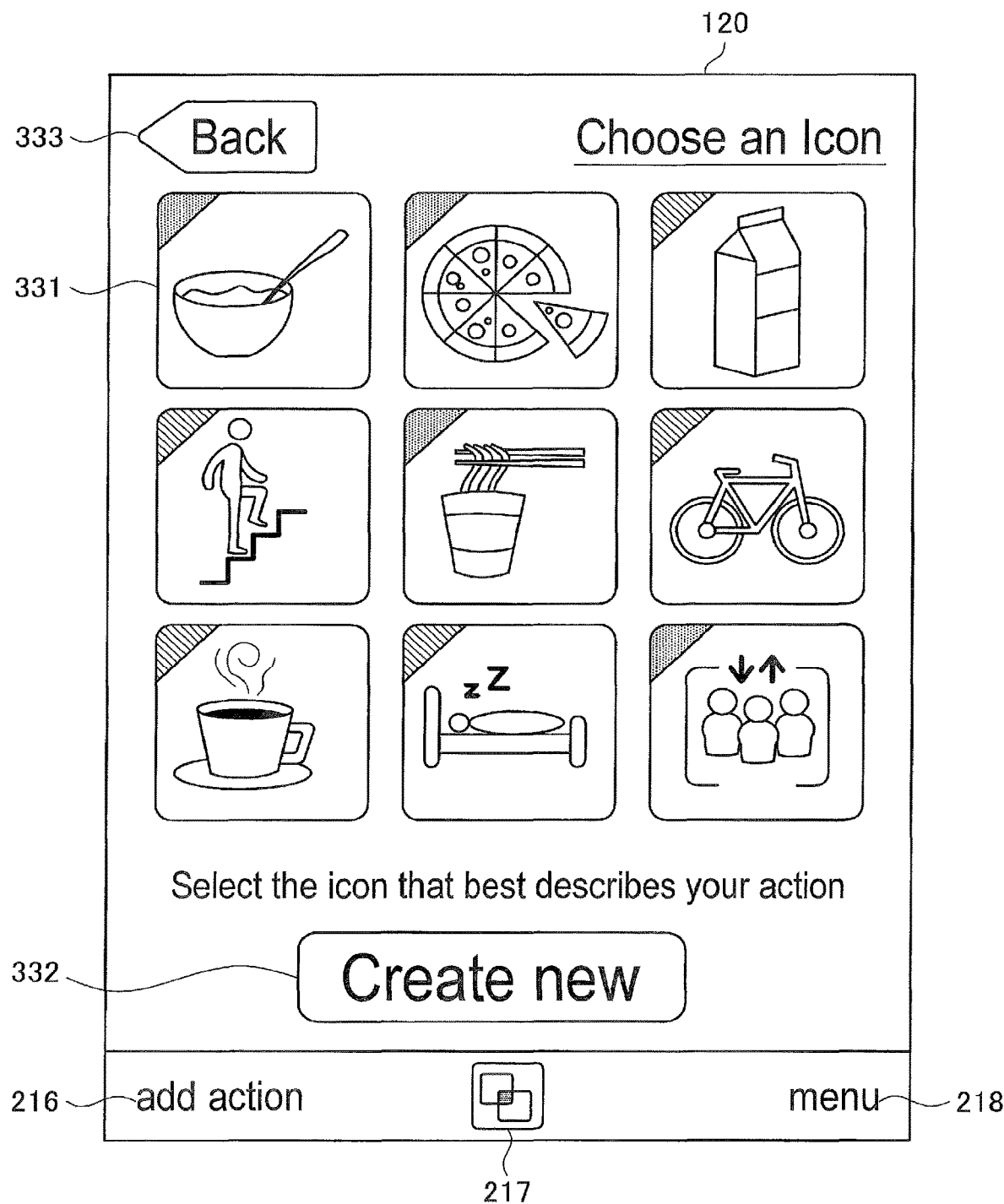
FIG. 19 is an explanatory diagram which shows an example of information displayed on a display section 120.

FIG. 19 is an explanatory diagram which shows an example of information displayed on the display section 120 of the portable terminal 100. The explanatory diagram shown in FIG. 19 is an example of an icon specification screen of the diet support application displayed on the display section 120 by transiting from the action addition screen of the diet support application shown in FIG. 18, in the case where the region 321 is selected by the user on the action addition screen of the diet support application shown in FIG. 18.

Icons 331 are displayed on the icon specification screen of the diet support application shown in FIG. 19. The icons 331 may be prepared in advance by the diet support application. The user of the portable terminal 100 can select an icon, from among the icons 331 displayed on the icon specification screen, which is appropriate for the action to be added on the action addition screen of the diet support application. When one of the icons 331 on the icon specification screen is specified by the user of the portable terminal 100, the diet support application may automatically return to the action addition screen of the diet support application shown in FIG. 18.

While a state is shown in FIG. 19 in which nine icons 331 are displayed on the display section 120, the present disclosure is not limited to such an example. Further, in the case where icons which the user can select are not able to be shown on one screen, the diet support application may switch, for example, to a page which displays the other icons by a flick operation or the like for the display section 120.

Note that, a case can be considered in which the user of the portable terminal 100 considers that there are no icons, among the icons prepared in advance by the diet support application, which are suitable for the action to be added at the action addition screen of the diet support application. When considering such a case, a button 332 for allowing the user of the portable terminal 100 to create a new icon is displayed on the icon specification screen of the diet support application shown in FIG. 19. By allowing the user of the portable terminal 100 to select the button 332, it is possible for the diet support application to create a new icon for the user of the portable terminal 100.

Further, a button 333 for returning to the action addition screen of the diet support application shown in FIG. 18 is displayed on the icon specification screen of the diet support application shown in FIG. 19. When the user of the portable terminal 100 selects the button 333 without specifying an icon, the diet support application may display the action addition screen of the diet support application prior to transition as it is on the display section 120.

In this way, when the user is allowed to freely create an icon, a situation can be considered in which a plurality of icons indicating a similar action are created by other users.

When considering such a situation, for example, if a similar action is indicated, the server apparatus 10 may retain the action registered by the user as a similar action even if there are different icons. For example, if there is a similarity to some extent in a keyword for an action, the server apparatus 10 may set the action as a similar action even if there are different icons.

Further, if icons indicating a similar action have already been created by other users, the server apparatus 10 may provide information of these already created icons to the portable terminal 100, and the diet support application may display the information of these already created icons acquired from the server apparatus 10.

The diet support application may have a function which allows the contents to be edited for the action registered by the user of the portable terminal 100 on the check in screen shown in FIG. 10.

Figure 20:
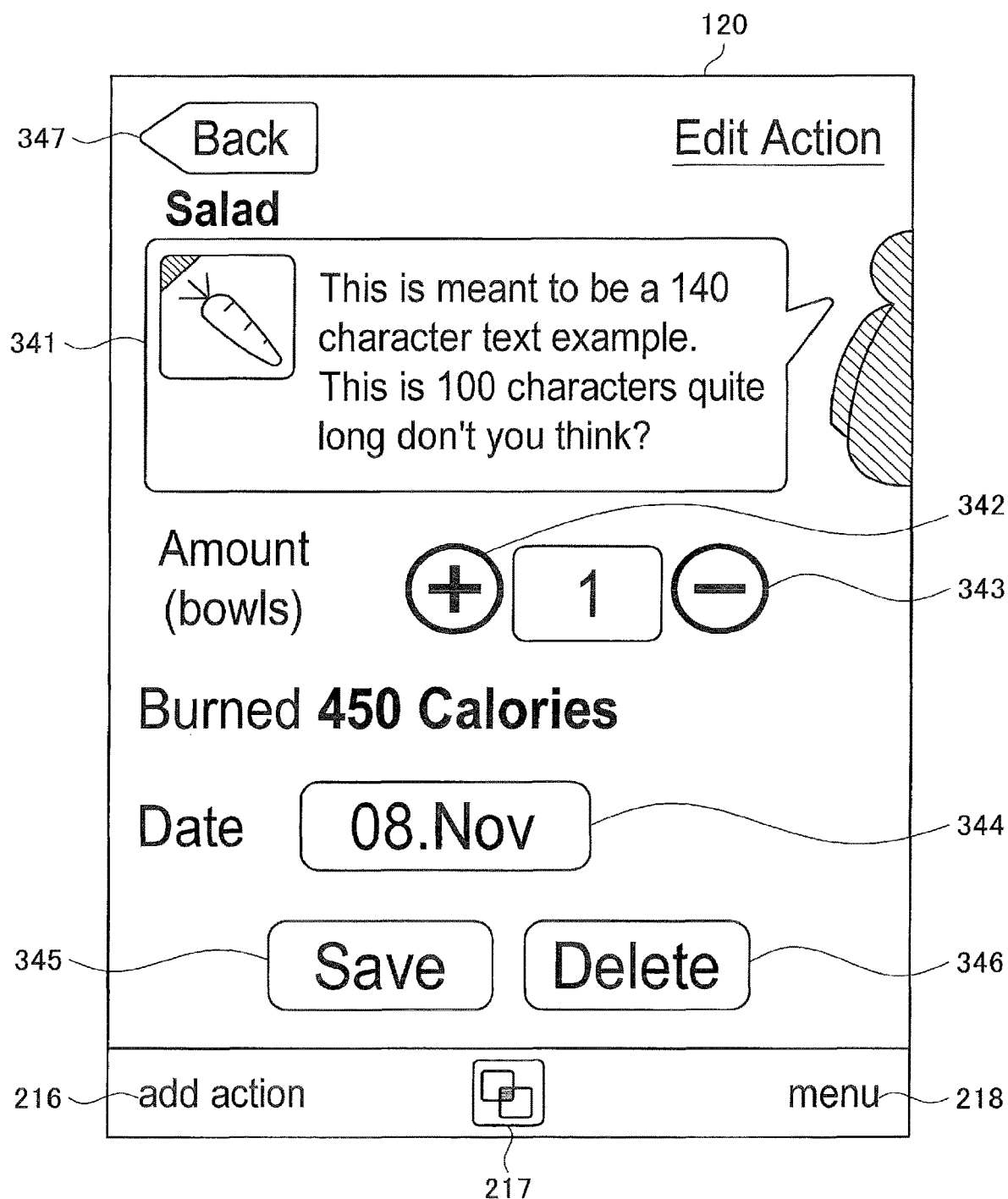
FIG. 20 is an explanatory diagram which shows an example of information displayed on a display section 120.

FIG. 20 is an explanatory diagram which shows an example of information displayed on the display section 120 of the portable terminal 100. The explanatory diagram shown in FIG. 20 is an example of an action edit screen of the diet support application displayed on the display section 120 by transiting from the timeline screen of the diet support application shown in FIG. 11, in the case where the region 265 is selected by the user of the portable terminal 100, for example, on the timeline screen of the diet support application shown in FIG. 11.

The contents of the action registered by the user of the portable terminal 100 are displayed on the action edit screen of the diet support application shown in FIG. 20, and a region 341 for editing this content, and buttons 342 and 343 for changing the amount of the action registered by the user of the portable terminal 100, are displayed on the action edit screen of the diet support application shown in FIG. 20. Further, a region 344 for changing the date of the action registered by the user of the portable terminal 100, a button 345 for saving the edited contents, and a button 346 for deleting the action registered by the user of the portable terminal 100, are displayed on the action edit screen of the diet support application shown in FIG. 20. Further, a button 347 for returning to the timeline screen of the diet support application shown in FIG. 11 is displayed on the action edit screen of the diet support application shown in FIG. 20.

By preparing the action edit screen such as shown in FIG. 20, the diet support application can allow the user of the portable terminal 100 to edit the contents of the temporarily registered action.

By using the diet support application, the user of the portable terminal 100 can accumulate, in the server apparatus 10, changes in the weight of the user himself or herself, and whether positive or negative actions are performed for the diet. Also, the diet support application can indicate the data accumulated in the server apparatus by the user of the portable terminal 100.

Figure 21:
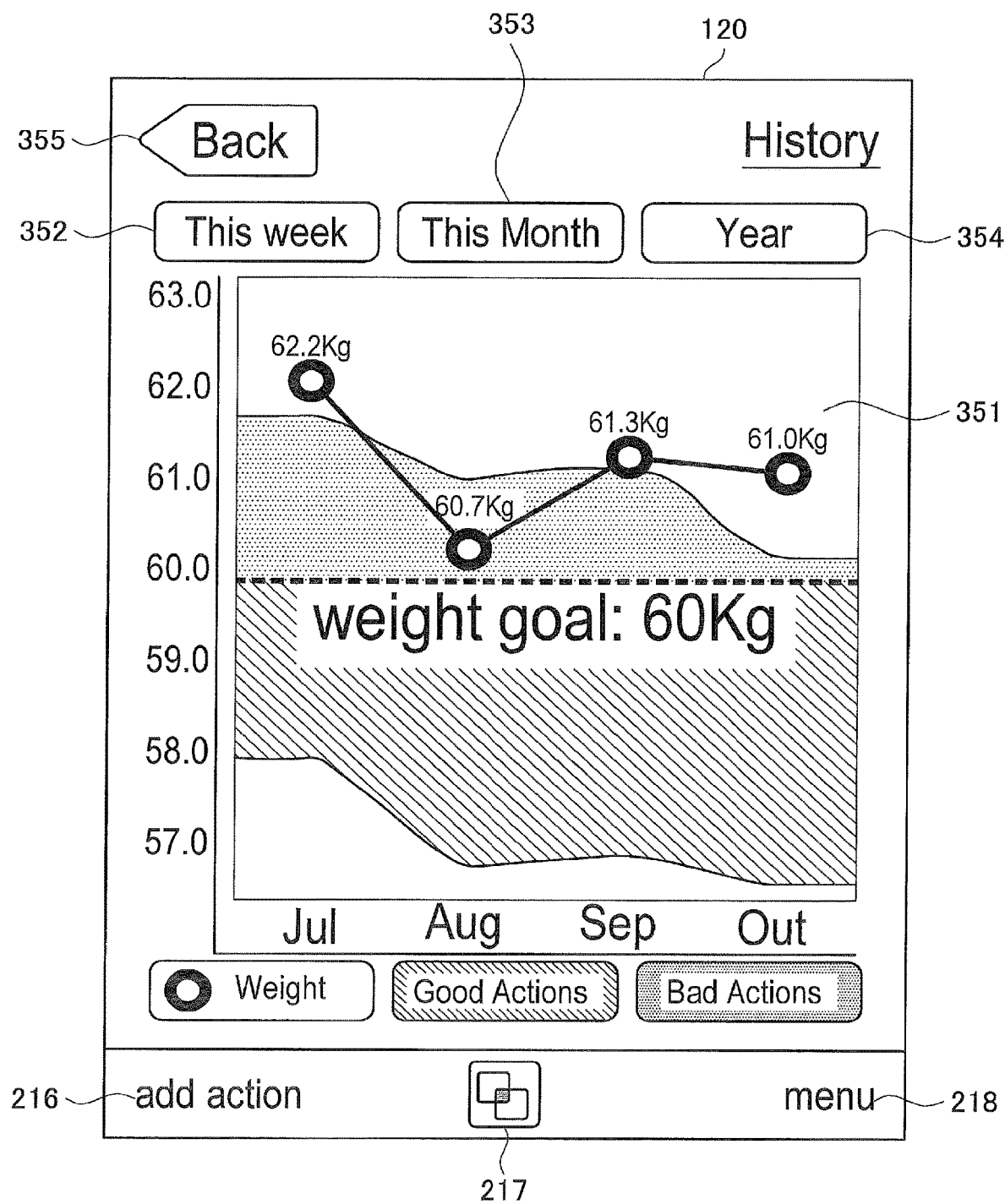
FIG. 21 is an explanatory diagram which shows an example of information displayed on a display section 120.

FIG. 21 is an explanatory diagram which shows an example of information displayed on the display section 120 of the portable terminal 100. The explanatory diagram shown in FIG. 21 is an example of a history screen displayed on the display section 120 by transiting from the main menu screen shown in FIG. 6, in the case where the button 213 is selected by the user of the portable terminal 100 on the main menu screen shown in FIG. 6.

A graph 351 which shows the data accumulated in the server apparatus 10 by the user of the portable terminal 100 is shown on the history screen of the diet support application shown in FIG. 21. In the example shown in FIG. 21, changes in the weight registered by the user of the portable terminal 100, and changes in the number of positive and negative actions for the diet registered by the user of the portable terminal 100, are shown in the graph 351. Further, a target weight registered by the user of the portable terminal 100 (in the example shown in FIG. 21, 60 kg) is also shown in the graph 351.

By setting the target weight registered by the user of the portable terminal 100 as a boundary for the change in the number of positive or negative actions for the diet in the graph 351 shown in FIG. 21, the diet support application may show the number of negative actions above the boundary and the number of positive actions below the boundary. This is because negative actions for the diet are actions connected to increasing weight, and positive actions for the diet are actions connected to decreasing weight.

Further, buttons 352, 353 and 354 for changing the display range of the horizontal axis of the graph are displayed on the history screen of the diet support application shown in FIG. 21. The functions of the buttons 352, 353 and 354 are similar to the functions provided by the buttons 232, 233 and 234 in the weight history screen of the diet support application shown in FIG. 8. Further, a button 355 for returning to the home screen is also displayed on the history screen of the diet support application shown in FIG. 21.

The diet support application may change the display form of the graph by allowing the user of the portable terminal 100 to touch the graph 351. For example, while changes in the number of positive or negative actions for the diet are shown in the graph 351 of FIG. 21, the diet support application may display, on the graph 351, changes of a value in which the number of negative actions are subtracted from the number of positive actions, in accordance with an operation of the user of the portable terminal 100. Further, for example, the diet support application may display only the changes in weight of the graph shown in FIG. 21, or only the changes in the number of actions, in accordance with an operation of the user of the portable terminal 100.

The diet support application may have a function which indicates whether such an action has been performed by the user in the past.

Figure 22:
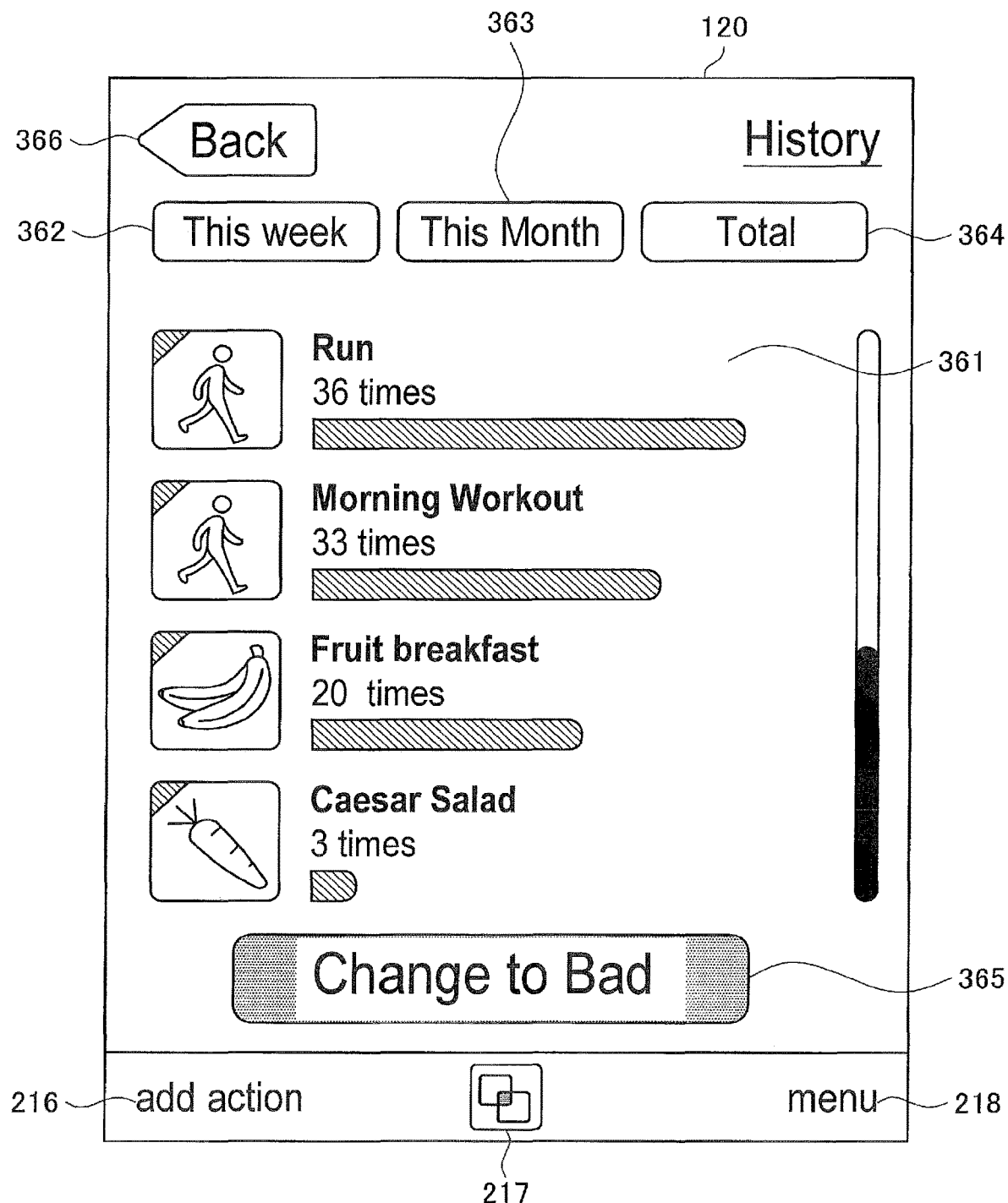
FIG. 22 is an explanatory diagram which shows an example of information displayed on a display section 120.

FIG. 22 is an explanatory diagram which shows an example of information displayed on the display section 120 of the portable terminal 100. The explanatory diagram shown in FIG. 22 is an example of another history screen of the diet support application displayed on the display section 120, for example, by transiting from the history screen of the diet support application shown in FIG. 21.

A region 361 which shows, by bar charts, how much of the positive actions for the diet have been registered by the user of the portable terminal 100 is displayed on the history screen of the diet support application shown in FIG. 22. In the example shown in FIG. 22, the region 361 shows, by bar charts, that running has been registered 36 times, a morning workout has been registered 33 times, a fruit breakfast has been registered 20 times, and a Caesar salad has been registered 3 times, by the user of the portable terminal 100. This region 361 may be enabled as a scrolling display in accordance with an operation of the operation section 130 by the user of the portable terminal 100.

Further, buttons 362, 363 and 364 for changing the total range of the bar graphs shown in the region 361 are displayed on the history screen of the diet support application shown in FIG. 22. The functions of the buttons 362, 363 and 364 are similar to the functions provided by the buttons 232, 233 and 234 in the weight history screen of the diet support application shown in FIG. 8.

Further, a button 365 for transiting to a screen which displays how much of the negative actions for the diet have been registered is displayed on the history screen of the diet support application shown in FIG. 22. Further, a button 366 for returning to the home screen is also displayed on the history screen of the diet support application shown in FIG. 22.

Figure 23:
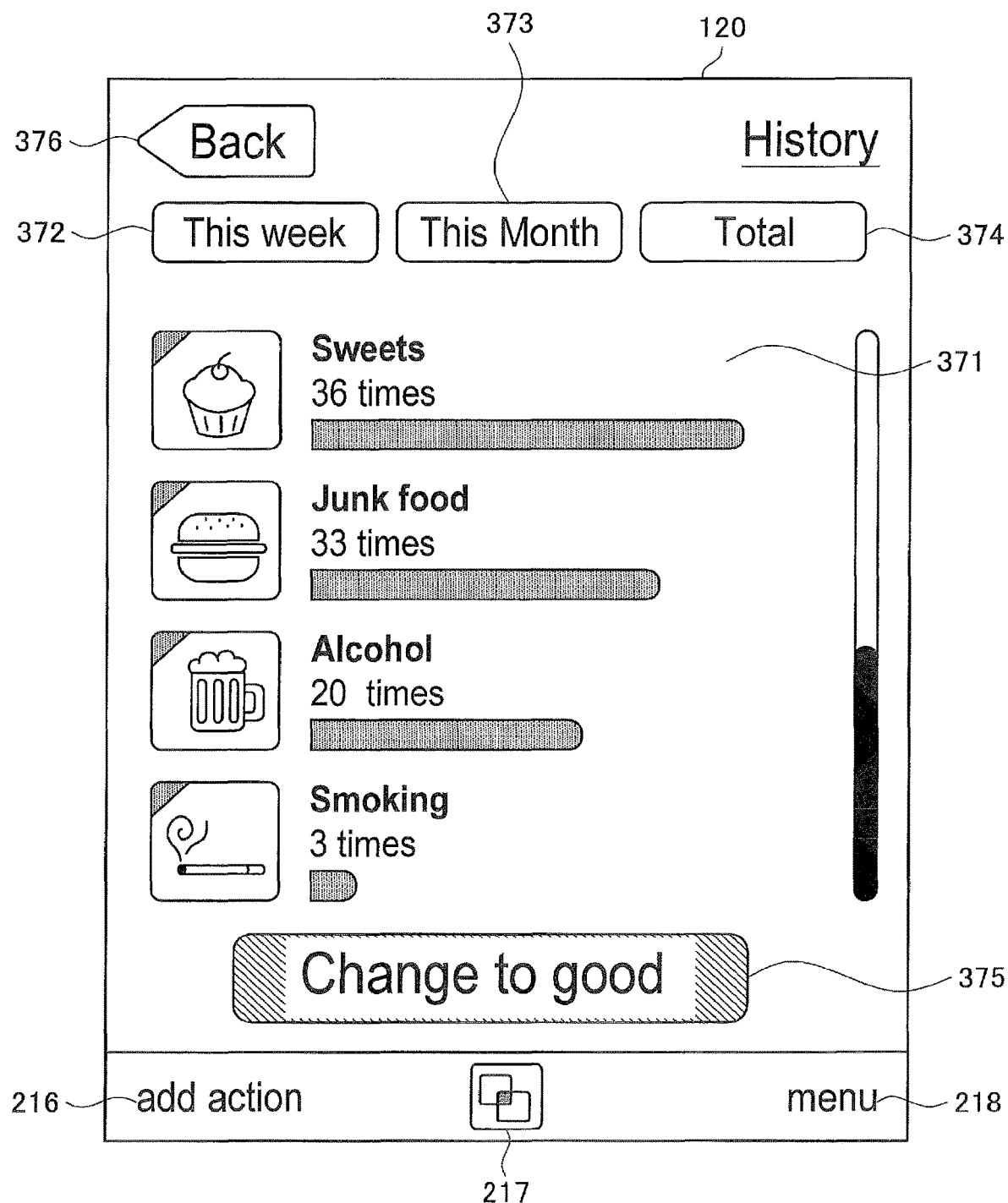
FIG. 23 is an explanatory diagram which shows an example of information displayed on a display section 120.

FIG. 23 is an explanatory diagram which shows an example of information displayed on the display section 120 of the portable terminal 100. The explanatory diagram shown in FIG. 23 is an example of another history screen of the diet support application displayed on the display section 120 by transiting from the history screen of the diet support application shown in FIG. 22, in the case where the button 365 is selected by the user of the portable terminal 100 on the history screen of the diet support application shown in FIG. 22.

A region 371 which shows, by bar graphs, how much of the negative actions for the diet have been registered by the user of the portable terminal 100 is displayed on the history screen of the diet support application shown in FIG. 23. In the example shown in FIG. 23, the region 371 shows, by bar charts, that eating sweets has been registered 36 times, eating junk food has been registered 33 times, drinking alcohol has been registered 20 times, and smoking has been registered 3 times, by the user of the portable terminal 100. This region 371 may be enabled as a scrolling display in accordance with an operation of the operation section 130 by the user of the portable terminal 100.

Further, buttons 372, 373 and 374 for changing the total range of the bar graphs shown in the region 371 are displayed on the history screen of the diet support application shown in FIG. 23. The functions of the buttons 372, 373 and 374 are similar to the functions provided by the buttons 232, 233 and 234 in the weight history screen of the diet support application shown in FIG. 8.

Further, a button 375 for transiting to the screen which displays how much of the positive actions for the diet have been registered, such as shown in FIG. 22, is displayed on the history screen of the diet support application shown in FIG. 23. Further, a button 376 for returning to the home screen is also displayed on the history screen of the diet support application shown in FIG. 23.

The diet support application may have a screen for editing information of the user who is using the diet support application.

Figure 24:
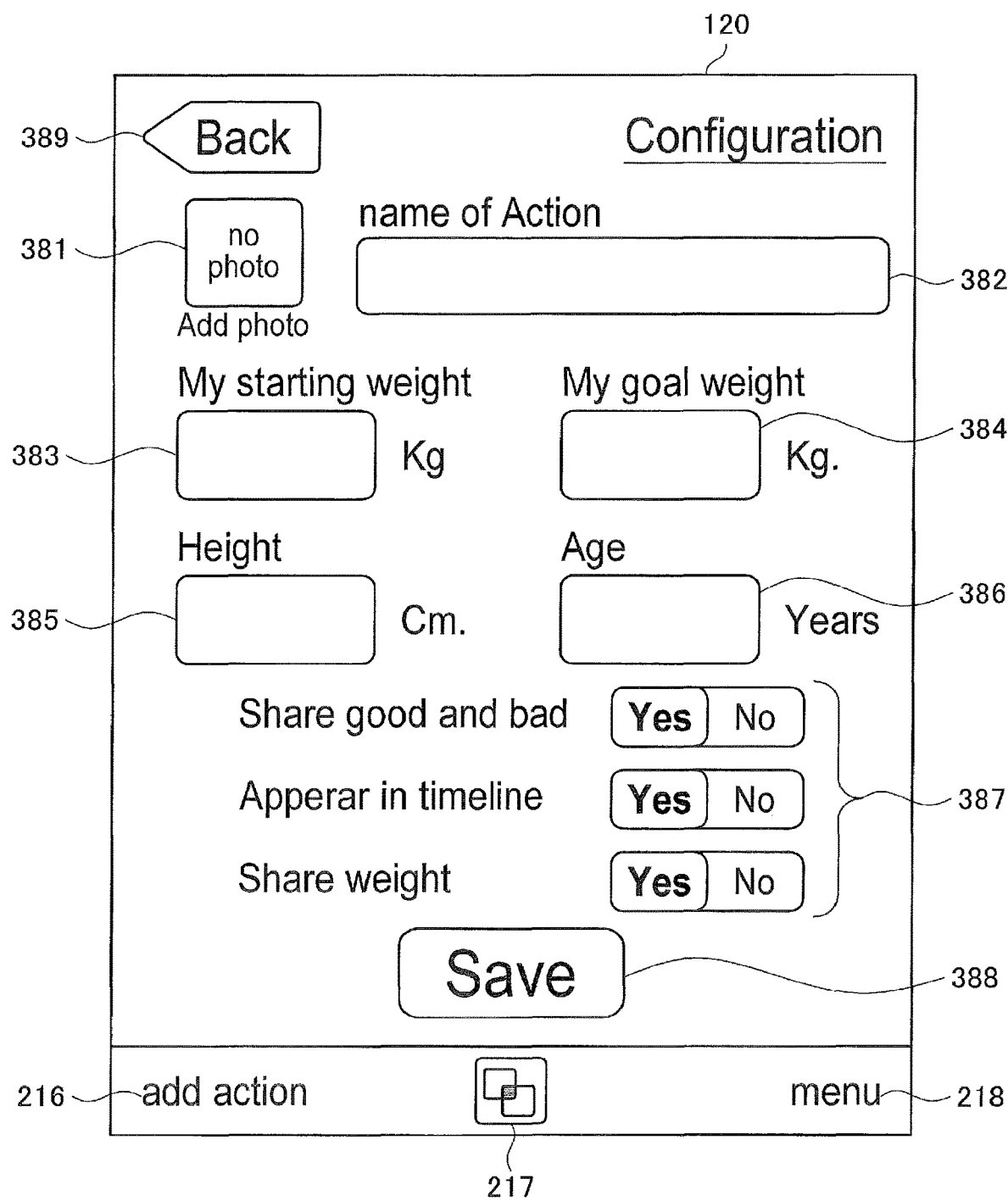
FIG. 24 is an explanatory diagram which shows an example of information displayed on a display section 120.

FIG. 24 is an explanatory diagram which shows an example of information displayed on the display section 120 of the portable terminal 100. The explanatory diagram shown in FIG. 24 is an example of a user information editing screen displayed on the display section 120 by transiting from the main menu screen shown in FIG. 6, in the case where the button 215 is selected by the user of the portable terminal 100 on the main menu screen shown in FIG. 6.

A region 381 which displays and allows editing of a profile image of the user, a region 382 which displays and allows editing of a username, a region 383 which displays and allows editing of a weight at the time when the diet is started, and a region 384 which displays and allows editing of a target weight, are displayed on the user information editing screen of the diet support application shown in FIG. 24. Further, a region 385 which displays and allows editing of a height of the user, a region 386 which displays and allows editing of an age of the user, and buttons 387 which allow settings for whether or not the contents registered by the user are to be shared with other users, are displayed on the user information editing screen of the diet support application shown in FIG. 24.

Further, a button 388 for allowing the edited contents to be saved, and a button 389 for returning to the main menu screen shown in FIG. 6, are displayed on the user information editing screen of the diet support application shown in FIG. 24.

By having the user information editing screen such as shown in FIG. 24, the diet support application can allow the user of the portable terminal 100 to edit the user information.

By having screens such as described above, the diet support application can maintain or improve motivation of the diet for the user who uses the diet support application.

It is needless to say that the screens shown in the figures referred to in the description up to here are merely examples, and the screens prepared by the application in the present disclosure are not limited to those shown in the FIGS. referred to in the description up to here. It is needless to say that the screens prepared by the application allow changes in a range which does not deviate from the technical idea of the present disclosure, and further, a range which does not deviate from the technical idea of the present disclosure is understood to belong to the technical range of the present disclosure even if such changes are made.

Hereinafter, modified examples of the screen of the diet support application executed by the portable terminal 100 according to an embodiment of the present disclosure will be described.

[Modified Examples]

Figure 25:
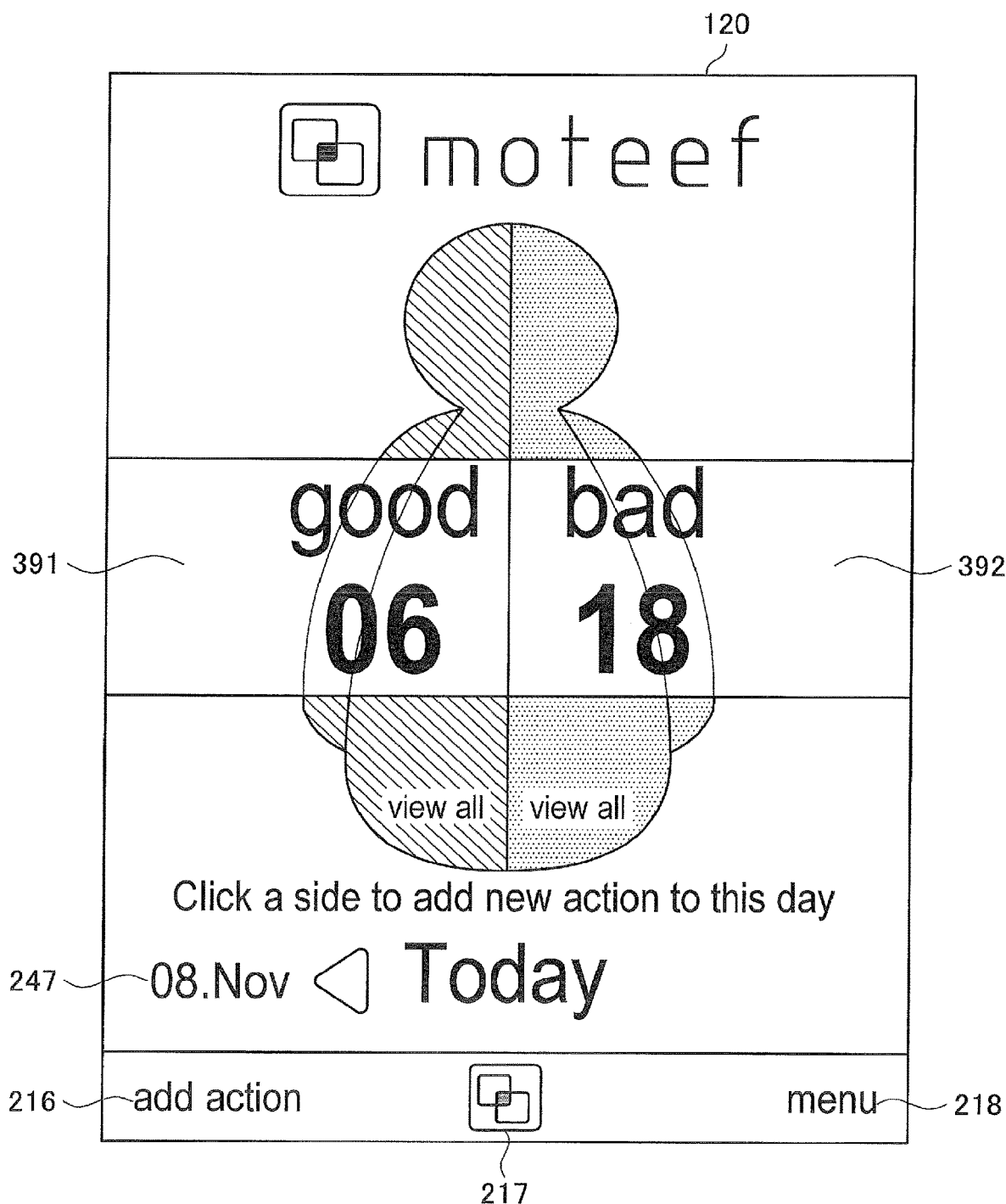
FIG. 25 is an explanatory diagram which shows an example of information displayed on a display section 120.

FIG. 25 is an explanatory diagram which shows an example of information displayed on the display section 120 of the portable terminal 100. The explanatory diagram shown in FIG. 25 is a modified example of the home screen of the diet support application displayed on the display section 120 by transiting from the main menu screen shown in FIG. 6, in the case where the button 211 is selected by the user of the portable terminal 100 on the main menu screen of the diet support application shown in FIG. 6.

A region 391 which displays the number of positive actions for the diet registered by the user, and a region 392 which displays the number of negative actions for the diet registered by the user, are displayed on the home screen of the diet support application shown in FIG. 25. The example shown in FIG. 25 shows that there are 6 positive actions and 18 negative actions for the diet registered by the user. Further, a region 247 for allowing the user to change the date on which an action is registered is shown on the home screen of the diet support application shown in FIG. 25, similar to that of the home screen shown in FIG. 9.

Figure 26:
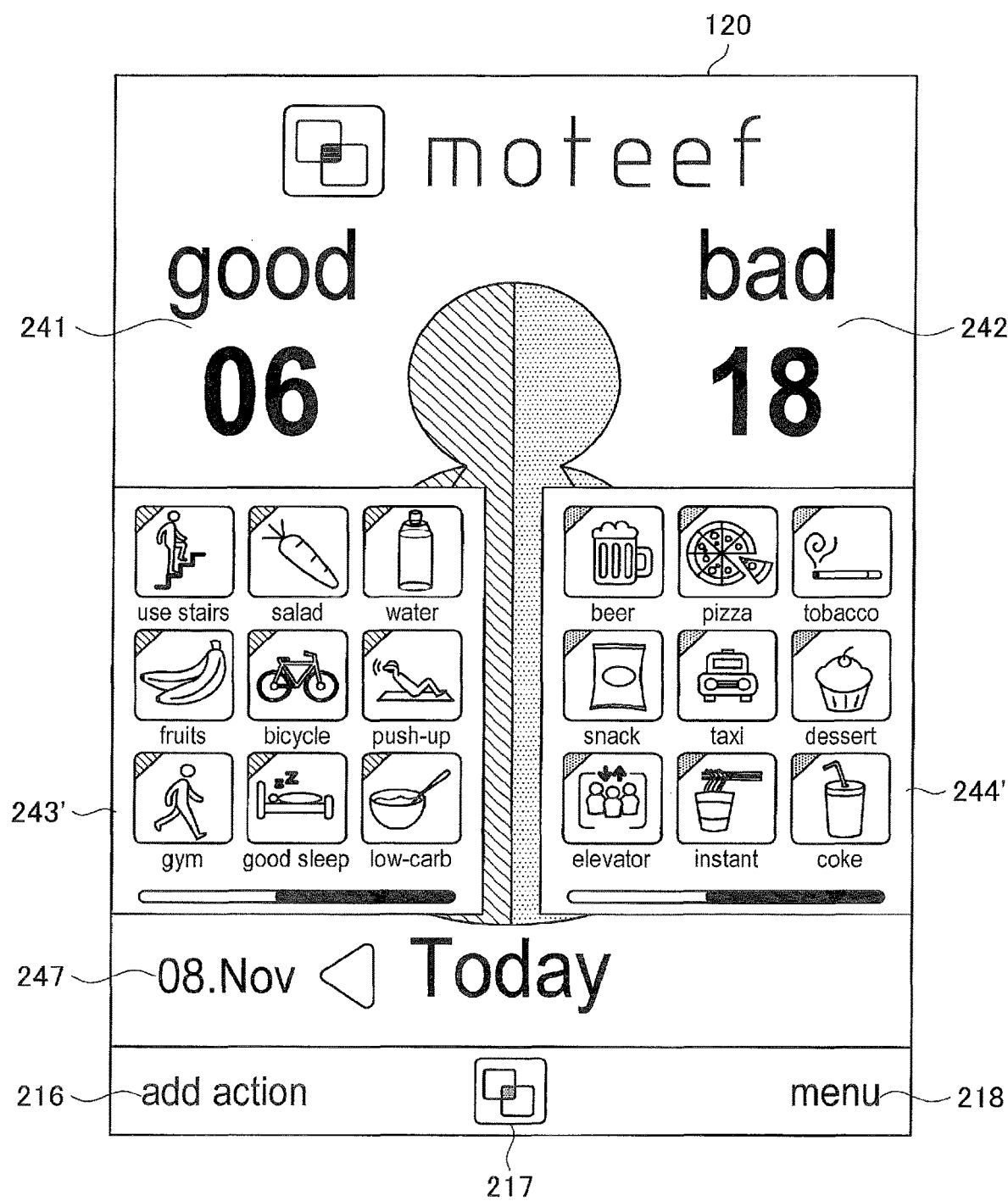
FIG. 26 is an explanatory diagram which shows an example of information displayed on a display section 120.

FIG. 26 is an explanatory diagram which shows an example of information displayed on the display section 120 of the portable terminal 100. The explanatory diagram shown in FIG. 26 is a modified example of the home screen of the diet support application displayed on the display section 120 by transiting from the main menu screen shown in FIG. 6, in the case where the button 211 is selected by the user of the portable terminal 100 on the main menu screen of the diet support application shown in FIG. 6.

A region 241 which shows the number of positive actions for the diet, and a region 242 which shows the number of negative actions for the diet, are displayed on the home screen of the diet support application shown in FIG. 26. Further, a region 243' which displays icons indicating positive actions for the diet, and a region 244' which displays icons indicating negative actions for the diet, are displayed on the home screen shown in FIG. 26.

The home screen of the diet support application shown in FIG. 26 is different from the home screen shown in FIG. 9 in that the icons are displayed in three columns in the regions 243' and 244'. By displaying such icons in three columns, the diet support application can display more icons on the home screen when compared to the home screen shown in FIG. 9.

Figure 27:
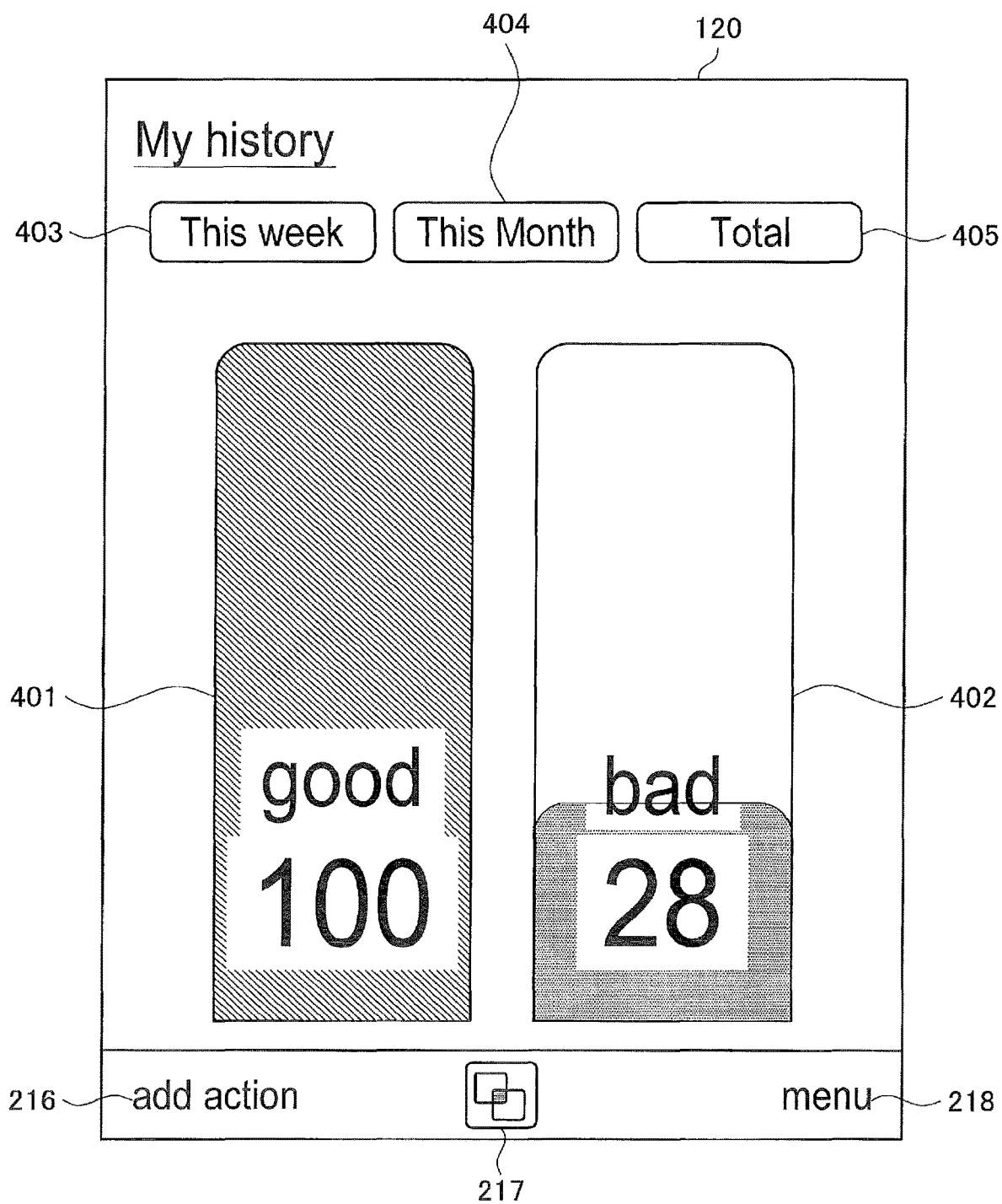
FIG. 27 is an explanatory diagram which shows an example of information displayed on a display section 120.

FIG. 27 is an explanatory diagram which shows an example of information displayed on the display section 120 of the portable terminal 100. The explanatory diagram shown in FIG. 27 is a modified example of the history screen displayed on the display section 120 by transiting from the main menu screen shown in FIG. 6, in the case where the button 213 is selected by the user of the portable terminal 100 on the main menu screen shown in FIG. 6.

Regions 401 and 402 which show, by bar graphs, data accumulated in the server apparatus 10 by the user of the portable terminal 100 are displayed on the history screen of the diet support application shown in FIG. 27. In the example shown in FIG. 27, the number of positive actions for the diet registered by the user of the portable terminal 100 is shown in the region 401. Further, the number of negative actions for the diet registered by the user of the portable terminal 100 is shown in the region 402.

Further, buttons 403, 404 and 405 for changing the total range of the bar graphs shown in the regions 401 and 402 are displayed on the history screen of the diet support application shown in FIG. 27. The functions of the buttons 403, 404 and 405 are similar to the functions provided by the buttons 232, 233 and 234 in the weight history screen of the diet support application shown in FIG. 8.

In this way, various modified examples of the screen displayed on the display section 120 by the diet support application can be considered. However, it is needless to say that the modified examples shown by the figures referred to in the description described above are merely examples, and the screens prepared by the application in the present disclosure are not limited to those shown in the figures referred to in the description up to here.

Up to here, examples of screens displayed on the display section 120 by the diet support application installed in the portable terminal 100 have been shown. The examples shown up to here are examples in which the user registers an action for the diet by selecting an icon displayed on the home screen of the diet support application in accordance with an intention of the user. When leaving such registration to the intention of the user, there is the possibility that the user will perform false registration, and the actual actions and the results of the diet may not necessarily be related to each other.

Accordingly, the diet support application may display icons on the home screen by using data acquired from another apparatus by the portable terminal 100, and may automatically register actions corresponding to these icons based on the acquisition of the data. For example, the diet support application may acquire data from a wearable apparatus worn by the user himself or herself, and may execute the display of icons and the registration of actions. In particular, since in the present embodiment it is desirable to maintain and improve motivation of the diet for the user, the diet support application can automatically register positive actions for the diet, by acquiring data from the wearable apparatus which can acquire a number of steps or distance travelled.

Figure 28:
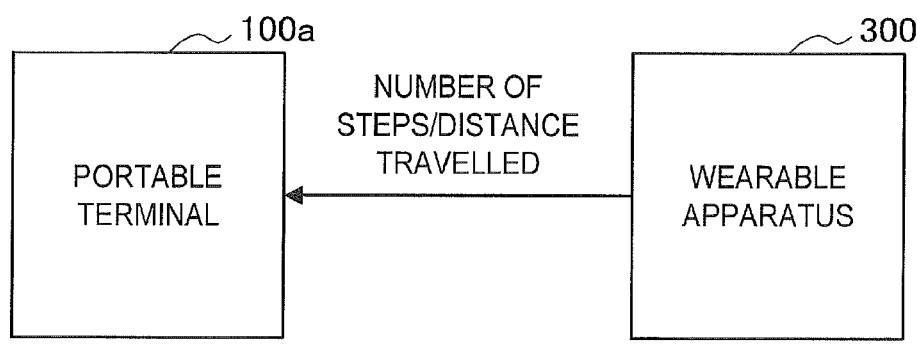
FIG. 28 is an explanatory diagram which shows a modified example of an embodiment of the present disclosure.

FIG. 28 is an explanatory diagram which shows a modified example of an embodiment of the present disclosure. FIG. 28 shows a state in which a portable terminal 100a used by the user acquires information, such as a number of steps or distance travelled, of the user from a wearable apparatus 300 which acquires the number of steps or distance travelled.

For example, it is assumed that data is acquired which indicates that the portable terminal 100a has travelled 5 kilometers from the wearable apparatus 300. From the data which indicates that 5 kilometers has been travelled, the diet support application may display, on the home screen, an icon which shows that 5 kilometers has been travelled, and may automatically register that 5 kilometers has been travelled as a positive action for the diet. Further, for example, in the case where an icon exists which shows that 5 kilometers has been travelled, when the portable terminal 100a acquires data which indicates that 10 kilometers has been travelled from the wearable apparatus 300, the diet support application may register that 10 kilometers has been travelled, by considering that the icon which shows that 5 kilometers has been traveled is selected two times.

In this way, by performing a display of icons and a registration of actions using the data acquired from another apparatus by the portable terminal 100a, the diet support application can attempt to maintain or improve motivation for the diet.

In the description up to here, the icons displayed on the home screen of the diet support application show positive or negative actions for the diet. The icons displayed on the home screen are not limited to those which show such actions for the diet. For example, the diet support application may display, as icons, advertisements of foods and drinks which are effective for the diet, or coupons with which these foods and drinks can be purchased cheaply. Further, for example, the diet support application may display, as icons, purchases of foods and drinks by the user which are effective for the diet. The display of such icons can be executed, for example, by registering purchases of products by the user in the server apparatus 10, and by acquiring a purchase history of products from the server apparatus 10 by the diet support application.

Further, for example, the diet support application may display, as icons, stamp information which shows that the user has participated in an event related to the diet, such as a sports event. For example, the diet support application may display, as an icon on the home screen, stamp information which can be acquired by the user participating in a walk rally. By displaying the diet support application on the home screen and selecting the icon which shows this stamp information, the user can register participation in the walk rally.

Further, for example, the diet support application may provide the user with a diet plan by combining specific actions. Also, the diet support application may provide the user with an incentive for the execution of this diet plan (for example, coupons or the like with which products effective for the diet can be purchased cheaply). The user can maintains or improves motivation for the diet by performing all of the actions included in the diet plan provided by the diet support application.

While the portable terminal 100 according to an embodiment of the present disclosure displays, on the display section 120, the screens shown in the figures referred to in the above described description, by executing the installed diet support application, the present disclosure is not limited to such examples. For example, a diet support service may be accessed which provides a service similar to the service provided by the diet support application, by a web browser installed in the portable terminal 100, and the screens shown in the figures referred to in the above described description may be displayed on the display section 120 by this web browser.

2. Conclusion

According to an embodiment of the present disclosure such as described above, a portable terminal 100 is provided which executes a diet support application capable of maintaining or improving motivation of a diet for a user. The diet support application executed by the portable terminal 100 allows a user to register actions for the diet, and to save these registered actions in a server apparatus 10 capable of being shared with other users. By sharing the actions for the diet with other users, an evaluation for these actions can be obtained from other users, and motivation for the diet can be maintained or improved for the user.

It may not be necessary for each step in the processes executed by each apparatus according to embodiments of the present disclosure to be performed in a time series process, in accordance with the order described in the sequence diagrams or flow charts. For example, each step in the processes executed by each apparatus may be performed in parallel, even if the processes are performed in an order different from the order described by the flow charts.

Further, a computer program for causing hardware, such as a CPU, ROM and RAM built-into each apparatus, to exhibit functions similar to the configurations of each of the above described apparatuses can be created. Further, a storage medium storing this computer program can also be provided. Further, a series of processes can be executed with the hardware, by configuring each of the functional blocks shown by the functional block figures with the hardware.

It should be understood by those skilled in the art that various modifications, combinations, sub-combinations and alterations may occur depending on design requirements and other factors insofar as they are within the scope of the appended claims or the equivalents thereof.

Additionally, the present technology may also be configured as below.

(1) An information processing apparatus, including:
an icon display section which displays an icon associated to an action of a user for a purpose of the user;
a selection condition acquisition section which acquires a selection condition of the icon displayed by the icon display section; and
a display information generation section which generates display information for sharing selected action associated to the icon with another user by using the selection condition acquired by the selection condition acquisition section.

(2) The information processing apparatus according to (1), wherein the selection condition acquisition section attaches an attribute to the selected action associated to the icon at a time when acquiring the selection condition of the icon.

(3) The information processing apparatus according to (2), wherein the attribute determines whether the action of the user is positive or negative about the purpose.

(4) The information processing apparatus according to any one of (1) to (4),
wherein the icon display section displays the icon in a state where an attribute is attached to the action of the user.

(5) The information processing apparatus according to any one of (1) to (4),
wherein the selection condition acquisition section counts a selection frequency of the icon by a contact frequency of the user of the icon.

(6) The information processing apparatus according to any one of (1) to (5), further including:
an information acquisition section which acquires information from another apparatus,
wherein the icon display section displays the icon by using information acquired from the another apparatus.

(7) The information processing apparatus according to (7),
wherein, based on the acquisition of information from the another apparatus, the selection condition acquisition section counts a selection frequency of the icon displayed by the icon display section by using the information acquired from the another apparatus.

(8) The information processing apparatus according to any one of (1) to (7),
wherein the icon display section displays an advertisement of products as the icon.

(9) The information processing apparatus according to any one of (1) to (8),
wherein the icon display section displays purchase of a product by the user as the icon.

(10) The information processing apparatus according to any one of (1) to (9),
wherein the icon displayed by the icon display section is capable of being created by the user.

(11) The information processing apparatus according to any one of (1) to (10),
wherein the display information generation section generates the display information by using the selection condition of the icon by the user and another prescribed user.

(12) An information processing method, including:
displaying an icon associated to an action for a purpose of a user;
acquiring a selection condition of the displayed icon; and
generating display information for sharing selected action associated to the icon with another user by using the acquired selection condition.

(13) A computer program for causing a computer to execute:
displaying an icon associated to an action for a purpose of a user;
acquiring a selection condition of the displayed icon; and
generating display information for sharing selected action associated to the icon with another user by using the acquired selection condition.

What is claimed is:

1. A non-transitory computer readable medium storing thereon a program that when executed by a computer causes the computer to execute a method comprising:
controlling a display to display a search condition input area into which an input search condition of a user action, registered in a server, is to be submitted,
to display an action list area including an action list having at least one action matching an input search condition, and
to display a detailed information area for an action selected from the action list;
controlling processing circuitry to register a selected good action in response to a user request in a registration area, wherein the registration area includes at least one of a name of the selected good action, calories burned by performance of the good action and save button image in a new action creation area;
generating a running count value of a total number of how many of the good actions were registered, wherein a good action is consistent with a user goal of achieving a goal weight and wherein a good action includes a good calorie burning activity and a good calorie consumption activity calorie burning activity and a good calorie consumption activity;

displaying a "good" label in association with the running count value of the total number of how many of the good actions were registered; and displaying the total number near the "good" label on a single screen instance on the display while also displaying an icon for each of the registered good actions including both an icon for the good calorie burning activity and an icon for the good calorie consumption activity, the icons displayed on the single screen instance.

2. The non-transitory computer readable medium according to claim 1, further comprising:

displaying the detailed information of the action in the detailed information area upon the user selection of the action from the action list.

3. The non-transitory computer readable medium according to claim 1, further comprising:

displaying, in the action list, an action name matching the search condition and calories consumed in the action.

4. The non-transitory computer readable medium according to claim 1, further comprising:

displaying the detailed information of the action and a button image for adding the action to the action log.

5. The non-transitory computer readable medium according to claim 1, further comprising:

displaying an icon for the action.

6. The non-transitory computer readable medium according to claim 1, further comprising:

displaying a user information edit area.

7. The non-transitory computer readable medium according to claim 6, further comprising:

controlling the processing circuitry to edit a privacy setting for sharing the user registered information in response to a user input in the user information edit area.

8. The non-transitory computer readable medium according to claim 7, further comprising: controlling processing circuitry to register a bad action.

9. The non-transitory computer readable medium according to claim 8, further comprising: generating a running count value of how many of the bad actions were registered.

10. A method comprising:

controlling a display to display a search condition input area into which a search condition of a user action, registered in a server, is to be submitted, to display an action list area including an action list having at least one action matching an input search condition, and to display a detailed information area for an action selected from the action list;

controlling processing circuitry to register a selected good action in response to a user request in a registration area, wherein the registration area includes at least one of a name of the selected good action, calories burned by performance of the good action and save button image in a new action creation area;

generating a running count value of a total number of how many of the good actions were registered, wherein a good action is consistent with a user goal of achieving a goal weight and wherein a good action includes a calorie burning activity and a good calorie consumption activity;

displaying a "good" label in association with the running count value of the total number of how many of the good actions were registered; and displaying the total number near the "good" label on a single screen instance on the display, while also displaying an icon for each of the registered good actions including both an icon for the good calorie burning activity and an icon for the good calorie consumption activity, the icons displayed on the single screen instance.

11. The method of claim 10, further comprising:

displaying the detailed information of the action in the detailed information area upon the user selection of the action from the action list.

12. The method of claim 10, further comprising:

displaying, in the action list, an action name matching the search condition and calories consumed in the action.

13. The method of claim 10, further comprising:

displaying the detailed information of the action and a button image for adding the action to the action log.

14. The method of claim 10, further comprising:

displaying an icon for the action.

15. The method of claim 10, further comprising:

displaying a user information edit area.

16. The method of claim 15, further comprising:

displaying a user information edit area.

17. The method of claim 16, further comprising:

controlling the processing circuitry to edit a privacy setting for sharing the user registered information in response to a user input in the user information edit area.

18. The method of claim 17, further comprising:

generating a running count value of how many of the bad actions were registered.

19. The method of claim 18, further comprising:

displaying the running count value of the bad actions next to the running count value of the good actions.

20. The non-transitory computer readable medium according to claim 9, further comprising:

displaying the running count value of the bad actions next to the running count value of the good actions.

* * * * *